United States Patent [19]

White

[11] Patent Number: 5,650,293
[45] Date of Patent: Jul. 22, 1997

[54] NUCLEIC ACID ENCODING PP60$^{PIK}$ AND THE METHODS OF MAKING PP60$^{PIK}$

[75] Inventor: Morris F. White, West Roxbury, Mass.

[73] Assignee: Joslin Diabetes Center, Inc., Boston, Mass.

[21] Appl. No.: 259,264

[22] Filed: Jun. 10, 1994

[51] Int. Cl.$^6$ .............................. C12P 21/06; C12N 5/00; C12N 1/20; C07H 21/04
[52] U.S. Cl. .................... 435/69.1; 435/354; 435/282.3; 435/320.1; 536/23.5
[58] Field of Search ........................ 536/23.5; 435/69.1, 435/240.2, 252.3, 320.1

[56] References Cited

U.S. PATENT DOCUMENTS

| | | | |
|---|---|---|---|
| 5,260,200 | 11/1993 | Kahn et al. | 435/68.1 |
| 5,434,064 | 7/1995 | Schlessinger et al. | 435/172.3 |

OTHER PUBLICATIONS

Escobedo et al "cDNA Cloning of a Novel 85 kd Protein . . . " *Cell* 65: 75–82 (Apr. 1991).
Skolnik et al "Cloning of PI3 Kinase . . . " *Cell* 65: 83–90 (Apr. 1991).
Otsu et al "Characterization of Two 85 kd Proteins . . . " *Cell* 65: 91–104.
Koyama et al "Structure of the PI3k SH3 Domain . . . " *Cell* 72 : 945–952 (Mar. 1993).
Dhand, R., et al., (1994) "PI 3–kinase: structural and functional analysis of intersbunit interactions", *The EMBO Journal*, vol. 13, No. 3, pp. 511–521.
Dhand, R. et al., (1984) "PI 3–kinase is a dual specificity enzyme: autoregulation by an intrinsic protein–serine kinase activity", *The EMBO Journal*, vol. 13, No. 3, pp. 522–533.
Kapeller, R., et al., (1994) "Identification of Two SH3–binding Motifs in the Regulatory Subunit of Phosphatidylinositol 3–Kinase", *The Journal of Biological Chemistry*, vol. 269, No. 3, pp. 1927–1933.
Pleiman, C.M., et al., (1994) "Activation of Phosphatidylinositol–3' Kinase by Src–Family Kinase SH3 Binding to the p85 Subunit", *Science*, vol. 263, pp. 1609–1612.
Klippel, A., et al., (1994), "The Interaction of Small Domains between the Subunits of Phosphatidylinositol 3–Kinase Determines Enzyme Actvity", *Molecular and Cellular Biology*, vol. 14, No. 4, pp. 2675–2685.
Hosomi, Y., et al., (1994) "Characterization of a 60–Kilodalton Substrate of the Insulin Receptor Kinase", *The Journal of Biological Chemistry*, vol. 269, No. 15, pp. 11498–11502.
Valius, M. and Kaslauska, A., (1993) "Phospholipase C–γ1 and Phosphatidylinositol 3 Kinase Are the Downstream Mediators of the PDGF Receptor's Mitogenic Signal", *Cell*, vol. 73, pp. 321–334.
Songyang, Z., et al., (1993) "SH2 Domains Recognize Specific Phosphopeptide Sequences", *Cell*, vol. 72, pp. 767–778.

Hu, P., et al., (1993) "Cloning of a Novel, Ubiquitously Expressed Human Phosphatidylinositol 3–Kinase and Identification of Its Binding Site on p85", *Molecular and Cellular Biology*, vol. 13, No. 12, pp. 7677–7688.
Prasad, K.V.S., et al., (1993) "Phosphatidylinositol (PI) 3–Kinase and PI 4–Kinase Binding to the CD4–p56$^{lck}$ Complex: the p56$^{lck}$ SH3 Domain Binds to PI 3–Kinase but Not PI 4–Kinase", *Molecular and Cellular Biology*, vol. 13, No. 12, pp. 7708–7717.
Wang, L.–M., et al., (1993) "IRS–1: Essential for Insulin–and IL–4–Stimulated Mitogenesis in Hematopoietic Cells", *Science*, vol. 261, pp. 1591–1594.
Lavan, B.E., and Lienhard, G.E., (1993) "The Insulin–elicited 60–kDa Phosphotyrosine Protein in Rat Adipocytes Is Associated with Phosphatidylinositol 3–Kinase", *The Journal of Biological Chemistry*, vol. 268, No. 8, pp. 5921–5928.
Sun, X.J., et al. (1993) "Pleiotropic Insulin Signals Are Engaged by Multisite Phosphorylation of IRS–1", *Molecular and Cellular Biology*, vol. 13, No. 12, pp. 7418–7428.
Sugimoto, S., et al., (1993) "Expression, Purification, and Characterization of SH2–containing Protein Tyrosine Phosphatase, SH–PTP2", *The Journal of Biological Chemistry*, vol. 268, No. 30, pp. 22771–22776.
Lechleider, R., et al., (1993) "Tyrosyl Phosphorylation and Growth Factor Receptor Association of the Human corskscrew Homologue, SH–PTP2", *Journal of Biological Chemistry*, vol. 268, No. 18, pp. 13434–13438.
Kelly, K.L., and Ruderman, N.B., (1993) "Insulin–stimulated Phosphatidylinositol 3–Kinase", *the Journal of Biological Chemistry*, vol. 268, No. 6, pp. 4391–4398.
Schu, P.V., et al., (1993) "Phosphatidylinositol 3–Kinase Encoded by Yeast VPS34 Gene Essential for Protein Sorting", *Science*, vol. 260, pp. 88–91.
Margolis, B., et al., (1992) "High–efficiency expression/cloning of epidermal growth factor–receptor–binding proteins with Src homology 2 domains", *Proceedings of the National Academy of Science*, vol. 89, pp. 8894–8898.
Sun, X.J., et al., (1992) "Expression and Function of IRS–1 in Insulin Signal Transmission", *The Journal of Biological Chemistry*, vol. 267, No. 31, pp. 22662–22672.
Myers Jr., et al., (1992) "IRS–1 activates phosphatidylinsitol 3'–kinase by associating with src homology 2 domains of p85", *Proceedings of the National Academy of Sciences*, vol. 89, pp. 10350–10354.
Backer J.M., et al., (1992) "Phosphatidylinositol 3'–kinase is activated by association with IRS–1 during insulin stimulation", *The EMBO Journal*, vol. 11, No. 9, pp. 3469–3479.
Zhang, B., and Roth, R., (1992) "The Insulin Receptor–related Receptor", *The Journal of Biological Chemistry*, vol. 267, No. 26, pp. 18320–18328.

(List continued on next page.)

*Primary Examiner*—Stephen G. Walsh
*Assistant Examiner*—Kenneth A. Sorensen
*Attorney, Agent, or Firm*—Louis Myers, Lahive & Cockfield

[57] ABSTRACT

A substantially pure nucleic acid comprising a sequence encoding a pp60$^{PIK}$ peptide and methods of using nucleic acid encoding pp60$^{PIK}$ to make pp60$^{PIK}$ polypeptide.

11 Claims, 16 Drawing Sheets

OTHER PUBLICATIONS

Mooney, R.A., and Bordwell, K.L., (1992) "Insulin Stimulates the Tyrosine Phosphorylation of a 61–Kiliodalton Protein in Rat Adipocytes", *Endocrinology*, vol. 130, No. 3, pp. 1533–1538.

Sun, X.J., et al., (1991) "Structure of the insulin receptor substrate IRS–1 defines a unique signal transduction protein", *Nature*, vol. 352, pp. 73–77.

Pons, S., et al., (1991) "Ontogeny of insulin–like growth factor I, its receptor, and its binding proteins in the rat hypothalamus", *Developmental Brain Research*, vol. 62, pp. 169–175.

Koch, C.A., et al., (1991) "SH2 and SH3 Domains: Elements That Control Interactions of Cytoplasmic Signaling Proteins", *Science*, vol. 252, pp. 668–673.

Thies, R.S., et al., (1990) "Insulin–Receptor Autophosphorylation and Endogenous Substrate Phosphorylation in Human Adipocytes From Control, Obese, and NIDDM Subjects", *Diabetes*, vol. 39, pp. 250–259.

Kaplan, D.R., et al., (1987) "Common Elements in Growth Factor Stimulation and Oncogenic Transformation: 85 kd Phosphoprotein and Phosphatidylinositol Kinase Activity", *Cell*, vol. 50, pp. 1021–1029.

Deng et al., "A novel expression vector for high–level synthesis and secretion of foreign proteins in Escherichia coli: overproduction of bovine pancreatic pholspholipase A2", Gene vol. 93:229–234, 1990.

```
p60^PIK   . . . . . . . . . . . . . . . . . . . . . . . . . . . . . . . . . . . . . . . . .
αp85      MSA.EGYQYRALYDYKKEREEDIDLHLGDILTVNKGSLVALGFSDGQEAKPEEIGWLNGY
βp85      -AGp--F-----PFRR--P--LE-LP--V-V-SRAA--Q---VAE-N-RC-QSV---MP-L p60^PIK   . . . . . . . . . . . . . . . . . . . . . . . . . . . . . . . . . . . . . . . . .
αp85      NETTGERGDFPGTYVEYIGRKKISPPTKPRPPRPLPVAPGPSKTEADSEQQASTLPDLA
βp85      --R-RQ---------FL-PVALAR-G-R---G-----AR-RDGPP-PGL.......---P p60^PIK   . . . . . . . . . . . . . . . . . . . . . . . . . . . . . . . . . . . . . . . . .
αp85      EQFAPPDVAPPLLIKLVEAIEKKGLECSTLY....RTQSSNPAELRQLLDCDTASLDLE
βp85      ---S------I-V------RT---DSYF PEppav--DW-LSDV-Q....WDAA-LS-GV p60^PIK   . . . . . . . . . . . . . . . . . . . . . . . . . . . . . . . . . . . . . . . . .
αp85      MFDVHVL.......ADAFKRYLLDLPNPVIPVAVSSELISLAPEVQSSEEYIQLLKKL
βp85      KGFLLA-paplvtpea-AEAH-A-REAAG--G-ALEPPT-PLHHALTLRF.....-QHp60^PIK   . . . . . . . . . . . . . . . . . . . . . . . . . . . . . . . . . . . . . . . . .
αp85      IRSPSIPHQYWLTLQYLLKIHF^KLSQTSSKNLLNARVLSELFSPLLFRFPA
βp85      G-VAGRAPAPGPAVRA-GAT-GP-LLRAPPPPSPPPGGAPDGTEPTPD--A p60^PIK   1 MYNTVWSMDRDDADWREVMPYSTELIFYIEMDPPALPPKPPKPMTPAVTNGMKDSFISL 60
αp85        ASS-NTEHLIKAIEILISTEWNERQPA---------T-V-N.--.NNNM--
βp85        LLVEKLLQEHLEEQEVA-------------TKPAPTGLANGG--PP---
```

FIG. 4

```
p60^PIK   61  QDAEWYWGDISREEVNDKLRDMPDGTFLVRDASTKMQGDYTLTLRKGGNNKLIKIYHRDG  120
αp85          ------------------E----TA-------------H-----------------F---
βp85          ------------------E----T--------------S-I-E--------------VFp60^PIK  121  KYGFSEPLTFTSVVELINHYHESLAQYNPKLDVKLTYPVSRFQQDQLVKEDNIDAVGKN   180
αp85          -------D--N-------RN--------------L---KY---V-----E----K
βp85          -------------C---D-T-R------------A---TR-L----KY----I---SVE----AQ p60^PIK  181  LQEFHSQYQEKSKEYDRLYEEYTRTSQEIQMKRTAIEAFNETIK|FEEQCHTQEQHSKDY  240
αp85          --H-YNT-F------R---------D--------------------Q---RY---E---
βp85          -KVY-Q---D--R---Q----------------L-------------GQ---KC---E--- p60^PIK  241  IERFRREGNEKEIERIMMNYDKLKSRLGEIHDSKLRLEQQLKKQALDNREIDKKMNSIKP  300
αp85          --K-K------T--Q---H--E------IS--V---RR-----E------AEY----R-
βp85          ---------------MQ--LL--SER------IA----E-RTK----E-RA---S-------R----L-- p60^PIK  301  DLIQLRKIRDQHLVWLNHRGVRQRRLNAWLGIKNEDSDESYFINEEDENLPHYDEKTWFV  360
αp85          --------T---Y-M---TQK----KK---E---NE-.-TE-Q.-SLV-D--D----H----N--
βp85          ------M------Y-----TQK-A---KKI-E---------TE-Q.--SLM-DEDD-----HE-R---Y-- p60^PIK  361  EDINRVQAEDLLYGKPDGAFLIRESSKKGCYACSVVADGEVKHCVIYSTARGYGFAEPYN  420
αp85          GSS---NK--N--R--R--T---V-----Q---------------V------NK--T---
βp85          GK----T-----EM-S--R--T--------QR--------------V-DT-----R--T-F-- p60^PIK  421  LYSSLKELVLHYQQTSLVQHNDSLNVRLAYPVHAQMPTLCR
αp85          ---------------H------------------T---Y--QRR---
βp85          --G---------HA-----------A-T-T--H--R-PG-GPPPAAR
```

FIG.4A

POTENTIAL TYR(P)-CONTAINING TRYPTIC PEPTIDES IN pp60

| PREDICTED CYCLE T V A | TRYPTIC PEPTIDE (TYR RESIDUE #) |
|---|---|
| 2 2 2 | MYNTVWSMDR (Y2) |
| 6 5 7<br>13 4 15 | EVMMPYSTELIFYIEMDPPALPPKPPKPMTPAVTNGMK (Y22,29) |
| 12 2 5 | DSFISLQDAEWYWGDISR (Y66) |
| 5 5 2 | MQGDYTLTLR** (Y100) |
| 2 2 3 | IYHR (Y116) |
| 1 1 2<br>9 5 19<br>27 5 27 | YGFSEPLTFTSVVELINHYHHESLAQYNPK (Y122,140,148) |
| 3 3 4 | LTYPVSR (Y158) |
| 9 5 9 | NLQEFHSQYQEK (Y188) |
| 2 2 2 | EYDR * (Y195) |
| 2 2 2<br>5 1 5 | LYEEYTRTSQEIQMK* (Y199,202) |
| 2 2 2 | DYIER* (Y240) |
| 5 5 5 | IMMNYDK* (Y260) |
| 8 2 4<br>20 5 7 | EDSDESYFINEEDENLPHYDEK** (Y341,353) |
| 8 4 4 | VQAEDLLYGKPDGAFLIR* (Y373) |
| 2 2 2 | GCYACSVVADGEVK (Y391) |
| 5 5 5 | HCVIYSTAR (Y407) |
| 2 2 2<br>8 2 8<br>11 8 11 | GYGFAEPYNLYSSLK* (Y413,419,422) |
| 6 5 6 | ELVLHYQQTSLVQHNDSLNVR (Y432) |
| 3 3 3 | LAYPVHAQMPTLCR (Y450) |

*FIG. 10A*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 5737 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1388..2749

( x i ) SEQUENCE DESCRIPTION: SEQ ID NO:1:

```
GGCACGAGCC AACCCCAAGC ACACTTCTGC CTGCTACTGT CTCTGAGCCC AGCACTACCT        60
CAGTGCCTGT AGAATCATCA CTGTTGTCTG GAGTTGTCAG GTCTACGAGG CCGCCTCCTA       120
CCCAGCCTGT GGTCCCCAGG CCCCACTTGG ACCCAAACTG GAACTCACAC AACAGTCCTG       180
TTCCCAGAGG ATGAGGACGA TGTATTGTTA TTGCCACTGG CTGAGCCAGA AGTCCTGGGT       240
TGGTGGAGGC AGAGGATGAA CCATTGCTTG CCTGAGGGAC TCTAGGCACA ATGGTATGAT       300
CCTTGGAAGT GGTTCAGCTT CCCCACTGAT CTATGTAGCA CAGAAAGTTA GTGTCTCTCC       360
AGCAGGGAGA GCATTCACTG TACACACCTT CTGGTATGAC AAGAGACTTC ACCACCACCC       420
TCTGCCCAGC CTGCTATCCA GGTGGCTGTG TTACAAAAGG TCCCACAAGG GTCACAGGCT       480
TGGACACTCC GTTCTTTCCA GCTCCCCACC CAAAAGTGGC CTTAACTACT AGACTGGTTG       540
GCTGGAGACC TAGCCACCAA GGGGAGGATT TGGCCAGGGT GATGGTTTTG CCAGCCTCCA       600
TCCCTGTGGT GCCTGGCCAC TTAGAGGACA CAAGTGCTTT TGCCCTGTAG CTGCATCATT       660
GTCCAGGAAA TCAAGATGAC AAAAATAAAG GAATCATAAA CTTCAGCCCT TGGTAAAAAA       720
AAACGGCACG AGGTTACCTT TACTACTCGG GCACAGTCGA GCTGACTGGA CTCTCCAAGG       780
GGTCGCCATC CCGAAGCTGC GGAAGCTTGG GTTCCAGCC TGACGCGAAT AGAGCCCGAG        840
TCCCAATCCC AGAGGGAATC GCTCTCCGCA GACCAGTGGG ACCCCGAAAC TTGAACGCAA       900
ACCCCCTTTT CAAGCCTTTG TCACTTCCCC AGCTTTCTCC CAACGCGTTC TTTTTCCCC        960
CTTCCTCTCC ATTCTCTCTT CTCCGAAGGA CACAAAGTG GCTTCCGCTG AAAGATTAGG       1020
AGGCGGTGGG AGCTTTTCCC TTTGGAGAGC GATTGTGTAG GAAGGATTTT CGGGAAGCTG      1080
CTTTTTAACA CCACTGCTCT TTGCTTTCCG AGCTTCCCTG TAACCCTCTG AGGTAAAAAC      1140
CCCGTAGCTT GAAAGTTCGG GGTATTTTGT TGGGTGCTTT AGGAGGAGAG AAGAGGAGGA      1200
CCTTGTCCTC ATCCTAGTAG TTTGGCTGGA CTTGTACTGG CCGTTGGAAA CCCCCAAGTA      1260
CATTTCCGTG TGGAACTTTT GCAAATATAT ATTTAGATTT TAAATATCAG ATAAAGATA       1320
TATATGCTTT TTATATATTT CCCGACGACC TGCCCCTGAC AGCGCGATGT ACAATACGGT      1380
```

```
GTGGAGT ATG GAC CGC GAT GAC GCA GAC TGG AGG GAG GTG ATG ATG CCC                  1429
        Met Asp Arg Asp Asp Ala Asp Trp Arg Glu Val Met Met Pro
        1               5                       10

TAT TCG ACA GAA CTG ATA TTT TAT ATT GAA ATG GAT CCT CCA GCT CTT                   1477
Tyr Ser Thr Glu Leu Ile Phe Tyr Ile Glu Met Asp Pro Pro Ala Leu
15              20                  25                  30

CCA CCA AAG CCA CCT AAG CCA ATG ACT CCA GCA GTC ACA AAT GGA ATG                   1525
Pro Pro Lys Pro Pro Lys Pro Met Thr Pro Ala Val Thr Asn Gly Met
                35                  40                  45

AAG GAC AGT TTC ATT TCT CTT CAA GAT GCA GAG TGG TAC TGG GGA GAT                   1573
Lys Asp Ser Phe Ile Ser Leu Gln Asp Ala Glu Trp Tyr Trp Gly Asp
            50                  55                  60

ATT TCC AGG GAA GAG GTA AAT GAC AAA TTG CGG GAC ATG CCA GAT GGT                   1621
Ile Ser Arg Glu Glu Val Asn Asp Lys Leu Arg Asp Met Pro Asp Gly
        65                  70                  75

ACC TTC TTA GTT CGT GAT GCC TCA ACG AAA ATG CAG GGG GAT TAT ACA                   1669
Thr Phe Leu Val Arg Asp Ala Ser Thr Lys Met Gln Gly Asp Tyr Thr
    80                  85                  90

TTG ACT TTG AGG AAG GGA GGA AAT AAT AAA TTA ATA AAG ATC TAT CAT                   1717
Leu Thr Leu Arg Lys Gly Gly Asn Asn Lys Leu Ile Lys Ile Tyr His
95                  100                 105                 110

CGG GAT GGT AAA TAT GGC TTC TCT GAG CCC CTG ACG TTT ACT TCT GTG                   1765
Arg Asp Gly Lys Tyr Gly Phe Ser Glu Pro Leu Thr Phe Thr Ser Val
            115                 120                 125
```

```
GTG GAG CTT ATT AAC CAC TAC CAC CAC GAG TCT CTC GCT CAG TAC AAT    1813
Val Glu Leu Ile Asn His Tyr His His Glu Ser Leu Ala Gln Tyr Asn
            130                 135                 140

CCC AAA CTC GAC GTG AAG CTG ACG TAC CCA GTA TCC AGA TTC CAA CAG    1861
Pro Lys Leu Asp Val Lys Leu Thr Tyr Pro Val Ser Arg Phe Gln Gln
        145                 150                 155

GAT CAG TTG GTA AAA GAA GAT AAC ATT GAT GCA GTA GGT AAA AAT CTG    1909
Asp Gln Leu Val Lys Glu Asp Asn Ile Asp Ala Val Gly Lys Asn Leu
        160                 165                 170

CAG GAG TTC CAC TCT CAG TAT CAG GAG AAG AGC AAA GAG TAT GAC AGG    1957
Gln Glu Phe His Ser Gln Tyr Gln Glu Lys Ser Lys Glu Tyr Asp Arg
175                 180                 185                 190

CTG TAT GAA GAG TAC ACA AGG ACA TCA CAG GAA ATA CAA ATG AAG AGG    2005
Leu Tyr Glu Glu Tyr Thr Arg Thr Ser Gln Glu Ile Gln Met Lys Arg
                195                 200                 205

ACT GCC ATT GAA GCC TTT AAT GAA ACA ATT AAA ATA TTT GAG GAG CAG    2053
Thr Ala Ile Glu Ala Phe Asn Glu Thr Ile Lys Ile Phe Glu Glu Gln
            210                 215                 220

TGT CAT ACC CAA GAA CAA CAC AGT AAA GAC TAT ATC GAG CGC TTT CGC    2101
Cys His Thr Gln Glu Gln His Ser Lys Asp Tyr Ile Glu Arg Phe Arg
        225                 230                 235

AGA GAG GGG AAT GAG AAG GAG ATC GAG CGA ATT ATG ATG AAT TAT GAT    2149
Arg Glu Gly Asn Glu Lys Glu Ile Glu Arg Ile Met Met Asn Tyr Asp
        240                 245                 250

AAA TTG AAA TCA CGT CTT GGT GAG ATT CAT GAT AGC AAA CTG CGT CTT    2197
Lys Leu Lys Ser Arg Leu Gly Glu Ile His Asp Ser Lys Leu Arg Leu
255                 260                 265                 270

GAG CAG GAC TTG AAG AAA CAA GCT TTG GAC AAC CGG GAA ATA GAT AAA    2245
Glu Gln Asp Leu Lys Lys Gln Ala Leu Asp Asn Arg Glu Ile Asp Lys
                275                 280                 285

AAA ATG AAT AGC ATC AAA CCC GAC TTG ATC CAG CTG CGT AAG ATC CGG    2293
Lys Met Asn Ser Ile Lys Pro Asp Leu Ile Gln Leu Arg Lys Ile Arg
            290                 295                 300

GAT CAG CAC CTT GTA TGG CTC AAT CAC AGA GGA GTG AGG CAG AGG CGC    2341
Asp Gln His Leu Val Trp Leu Asn His Arg Gly Val Arg Gln Arg Arg
        305                 310                 315

CTG AAT GCC TGG CTG GGG ATC AAG AAT GAG GAC TCA GAT GAA AGC TAT    2389
Leu Asn Ala Trp Leu Gly Ile Lys Asn Glu Asp Ser Asp Glu Ser Tyr
        320                 325                 330

TTT ATC AAT GAG GAA GAT GAG AAC CTG CCG CAT TAT GAT GAG AAA ACC    2437
Phe Ile Asn Glu Glu Asp Glu Asn Leu Pro His Tyr Asp Glu Lys Thr
335                 340                 345                 350

TGG TTT GTG GAG GAT ATC AAC CGA GTA CAA GCA GAG GAC TTG CTT TAT    2485
Trp Phe Val Glu Asp Ile Asn Arg Val Gln Ala Glu Asp Leu Leu Tyr
                355                 360                 365

GGG AAA CCA GAT GGT GCA TTC TTA ATT CGT GAG AGT AGC AAG AAA GGA    2533
Gly Lys Pro Asp Gly Ala Phe Leu Ile Arg Glu Ser Ser Lys Lys Gly
            370                 375                 380

TGT TAC GCT TGT TCT GTG GTT GCA GAC GGG GAA GTG AAG CAC TGT GTC    2581
Cys Tyr Ala Cys Ser Val Val Ala Asp Gly Glu Val Lys His Cys Val
        385                 390                 395

ATC TAC AGC ACG GCT CGA GGA TAT GGC TTT GCA GAA CCC TAC AAC CTG    2629
Ile Tyr Ser Thr Ala Arg Gly Tyr Gly Phe Ala Glu Pro Tyr Asn Leu
        400                 405                 410

TAC AGC TCA CTG AAG GAG CTG GTG CTC CAT TAC CAG CAG ACA TCC CTG    2677
Tyr Ser Ser Leu Lys Glu Leu Val Leu His Tyr Gln Gln Thr Ser Leu
415                 420                 425                 430

GTT CAG CAC AAC GAC TCC CTC AAC GTC AGG CTC GCC TAC CCT GTC CAT    2725
Val Gln His Asn Asp Ser Leu Asn Val Arg Leu Ala Tyr Pro Val His
                435                 440                 445
```

```
GCA CAG ATG CCT ACG CTC TGC AGA TAAGCAGAGT GGAAGAGACA CACTCTCTAG   2779
Ala Gln Met Pro Thr Leu Cys Arg
            450

CCGTTTTTTT CCTATGGTTT TTATTAGACT ACGATGAGGG CATTCTTTCA ACGTAGACTG   2839

CTTGTTTGCA CAAGTGATTC TGTGAATGTG AAATGGAGAG GCCAAGCAGT AGCTTGGATT   2899

TAGAAATGAG GGGCCCAGGG TCTCTGGCCT CGGCTGTGCT GCTGCACTGA TGGACTAAGC   2959

TGGAAGCAGA TATTGGTTTC ATGGGGTTTG GGTTTGTTGT CAGGCACCTT TAAAAGAACA   3019

GCTAAGGCTT GTTGTGGGTT GGGGTGGGGG TTTTATTTGG AAGTTTCTGA AGAGTCCACA   3079

TCCCTTTGTC CTCAACCCTA AGAATGCAGC AGGTCACAGT TCTGCTGGGA GTTGTTTTGA   3139

TTTGATAGTC TCTTCCCCTT TCCCCCAAAT AAAGAGCCGA TTTTGGCTCT GTGGTAAAGT   3199

GGGATTTGGT TTGGAGGGAA AAACAACCAA AGGAAAATAG GAGGTATGG GATTACATTT   3259

TCAGAATCTA AACCAAGGAG GCAAAAGACC CCTTCAGTTG ATGTTACTTC AATTTTATCA   3319

ACATAATCTA GGCTTCAGCA TCTTCACCAA CTCCTCCCTC TAAAGCACTG TGTTCAAAAA   3379

CCAACAAAGC AGCATCGCCN AGACCAAGGT CTAAGGGAG GACAGTAGTA GCTGAATGTA   3439

CACTTCTGTA CCAAAACTTG AAAGACTAGA AATGTGAGTT TCAACAAACA CTAAAATTGG   3499

TCAGTGTATT TCCTTTTGCC CTGGCCTTGT TTCTCAGATG AGGAATAGAA TTATTTTGTG   3559

GAAATAGTAA GCTTGAGTC ATAATGAAGT TGGTGCTTGT GTGGTGTTTC TTTAAAGAAA    3619

TGTTTGAAAC CCTTGTAAGT TGTTTATGA GTAAAGAAAC AGTGCAATCC AGTGCTTTA    3679

GATGGCTTGA TATACCAAAT AATGATAGAG AACAACATTG TTGTGTGCTT CCTCAAGTTT   3739

AAAAGCCTTG CCAAAACTAT ACAAGGATTA ATTTGCCTTC ATCTCCCCTT CCTTTTTTGG   3799

ATAGGGTTTA GGGAGCCATA GGTAGCTAAA GGAGGACTCG AGTTTGTGGT CAGAGACCTC   3859

AGTAAATCAC AGGCACATGA GGCCTGGTAT CCATGGTGAA GGGTCCATCA CATGACATGT   3919

TATTCAATAC TGTGGTTGAA GCGTTTGCCA GAAGAGGGGA TGACGTGGAG TTCAGACTAT   3979

CTGGGGAAAT AATCCACAGG CTTTCCTGCT TGCCCTTTTT GTGAGCCTGC TGTTAAGGCA   4039

GTGCACACAG CCTGCTCTCA TGCTTCCGTG GCTGTGGTTT AAGCCTTCAG CTAAGTGAAG   4099

TTAGATAGAG GAGAGGGCAG CCATCTATTT ATGGATTCAC ACTCATTTAA GAGTTCAGCT   4159

GCTTCAGAGT CAGTTCTGGA GCCATAACAG GCTCAGTATG ACTCAGCTGC TTGAGCCCAG   4219

TAATGTGCAG TCAGGCAGTT TAGACAAGCA GCCTGTGCCT GGGTCATCAG GCTTACAATC   4279

AGGGAAGATG AAGTTTGGGG GCCAAAATAA AGATGAATAT GACTTTCCCT GAGCACTTCC   4339

TTTGGTGACA GTGTCTAGAA GAAACCACAG TATAGAGATA GGTCAAAAGT TTTGAATAAT   4399

TGTCACAGTT GATAGGGCAT GCCATTGATG GCTTTTCTT GTTCATGCTC CAGTGTGAAA    4459

GAGAGGAGAT TGACCACCCT CAGCCACTCT GTAAGGCCTT TTTCAAAATT GCCAGCTTAA   4519

AATCTTGCTC AGTTACCAA GTAATGCCAG GCTATTGTT GATTGGAATA CCTGTGACTT     4579

TGTACTGATG TTGAACTTGC TGAAGCAGTT ATATGCTCAA GATTAGGTGT GAGGAATCCC   4639

TCTGATCCAG CACTAAAATT TTAGTATGTC CTGAACGCCT TTTTAAAGAA ATCTCTTCCA   4699

AGTAAGTCAA AATGATAAAA TATACAGCTT TAGTGTTGAA TAATGTCTTT ACCTTGTAGG   4759

CAGACATGGA AGATATGCAG GAGAAAGCAG CATCTACACC TGGGCTGGAC AATGGAGAAA   4819

GACAGGTTTT CAGTCCTATA TTCTTTCCCT TTGAGTAACC ACTTTGTGGG AGCTGAGACC   4879

AGGGATCATT TAATAAATCG GAAGCTATCT TTTTATTTTT CTGCCAAGTT ACTACATGAT   4939

TTATCTGATC CTGAGCTGTG GAAATGGCAT GAGGAGCAGT CTCCTAAGAG TGGCCCTGCT   4999

GTCTGAGGGA GTCTGGAAGC AGGTGTTGGT CTTCTTCTCA AGGCTAGCTC AAAGTTCTGT   5059
```

-continued

```
CTCATGATCT AGGCCCTGGG ACTATCTCTT TTGGCATCTT AACTGTAGAC TCATTGACTA      5119
AAGCAGAGGC TAGAGACAGA TTAGGACCAT AGGGGCAGGC AGATCAGCCA GTCCCCAGAT      5179
CAGCCAGTCC CCAACAGGAA AGCAGCTTTG GGTTGGCTAG ATACAGTTTT TAAAATAAAA      5239
ACAAAACAAA ACAAAGCTGT TTCCACCTGG CATAGTTCAG CTTAGGTAGG TTGTTTATGT      5299
TCTTGTCACT GCTCCAGCAA TAGATGAAGA CATCCTACAG CTCCACACTA CTAAGACACA      5359
AGCTCTCTAC ATTTACTTCA GACTCAAGCC CGAGTGGCAT CTTCCTTGTG TCCCTTCTCT      5419
GCAAGGTACC AGCTTCACCC ATTCTCCAGA ACTTTAAAGA AAAATGTAC TTGAACAATT       5479
TCTGATTTCT AGGATGATCT CTACTGCCAG TTAGATCTTC TTGAGGTTTC CATGACATCA      5539
TACACCAGAG GTCCATTCTT GGTCCTTTGC TGCCAACTGC TCATTCTTGA CTTAGCTCTA      5599
GCCATTTGTG ACAACCACCC TTGTTTCCTT ACAAATCCTC GCATGTAACT TTGGTACTTT      5659
GTTGTTTCTT GTGAAGAATC TATTCTGTTG TCTTTGATGT AATAAAAAAA TTTCATGTAA      5719
AAAAAAAAAC TCGTGCCG                                                    5737
```

( 2 ) INFORMATION FOR SEQ ID NO:2:

( i ) SEQUENCE CHARACTERISTICS:
        ( A ) LENGTH: 454 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Asp Arg Asp Asp Ala Asp Trp Arg Glu Val Met Met Pro Tyr Ser
  1               5                  10                  15
Thr Glu Leu Ile Phe Tyr Ile Glu Met Asp Pro Pro Ala Leu Pro Pro
             20                  25                  30
Lys Pro Pro Lys Pro Met Thr Pro Ala Val Thr Asn Gly Met Lys Asp
         35                  40                  45
Ser Phe Ile Ser Leu Gln Asp Ala Glu Trp Tyr Trp Gly Asp Ile Ser
     50                  55                  60
Arg Glu Glu Val Asn Asp Lys Leu Arg Asp Met Pro Asp Gly Thr Phe
 65                  70                  75                  80
Leu Val Arg Asp Ala Ser Thr Lys Met Gln Gly Asp Tyr Thr Leu Thr
                 85                  90                  95
Leu Arg Lys Gly Gly Asn Asn Lys Leu Ile Lys Ile Tyr His Arg Asp
            100                 105                 110
Gly Lys Tyr Gly Phe Ser Glu Pro Leu Thr Phe Thr Ser Val Val Glu
        115                 120                 125
Leu Ile Asn His Tyr His His Glu Ser Leu Ala Gln Tyr Asn Pro Lys
    130                 135                 140
Leu Asp Val Lys Leu Thr Tyr Pro Val Ser Arg Phe Gln Gln Asp Gln
145                 150                 155                 160
Leu Val Lys Glu Asp Asn Ile Asp Ala Val Gly Lys Asn Leu Gln Glu
                165                 170                 175
Phe His Ser Gln Tyr Gln Glu Lys Ser Lys Glu Tyr Asp Arg Leu Tyr
            180                 185                 190
Glu Glu Tyr Thr Arg Thr Ser Gln Glu Ile Gln Met Lys Arg Thr Ala
        195                 200                 205
Ile Glu Ala Phe Asn Glu Thr Ile Lys Ile Phe Glu Glu Gln Cys His
    210                 215                 220
Thr Gln Glu Gln His Ser Lys Asp Tyr Ile Glu Arg Phe Arg Arg Glu
```

```
225                      230                      235                      240

Gly Asn Glu Lys Glu  Ile Glu Arg Ile Met  Met Asn Tyr Asp Lys  Leu
                245                  250                  255

Lys Ser Arg Leu Gly  Glu Ile His Asp Ser  Lys Leu Arg Leu Glu  Gln
                260                  265                  270

Asp Leu Lys Lys Gln  Ala Leu Asp Asn Arg  Glu Ile Asp Lys Lys  Met
            275                  280                  285

Asn Ser Ile Lys Pro  Asp Leu Ile Gln Leu  Arg Lys Ile Arg Asp  Gln
        290                  295                  300

His Leu Val Trp Leu  Asn His Arg Gly Val  Arg Gln Arg Arg Leu  Asn
305                  310                  315                       320

Ala Trp Leu Gly Ile  Lys Asn Glu Asp Ser  Asp Glu Ser Tyr Phe  Ile
                325                  330                  335

Asn Glu Glu Asp Glu  Asn Leu Pro His Tyr  Asp Glu Lys Thr Trp  Phe
            340                  345                  350

Val Glu Asp Ile Asn  Arg Val Gln Ala Glu  Asp Leu Leu Tyr Gly  Lys
        355                  360                  365

Pro Asp Gly Ala Phe  Leu Ile Arg Glu Ser  Ser Lys Lys Gly Cys  Tyr
    370                  375                  380

Ala Cys Ser Val Val  Ala Asp Gly Glu Val  Lys His Cys Val Ile  Tyr
385                  390                  395                       400

Ser Thr Ala Arg Gly  Tyr Gly Phe Ala Glu  Pro Tyr Asn Leu Tyr  Ser
                405                  410                  415

Ser Leu Lys Glu Leu  Val Leu His Tyr Gln  Gln Thr Ser Leu Val  Gln
            420                  425                  430

His Asn Asp Ser Leu  Asn Val Arg Leu Ala  Tyr Pro Val His Ala  Gln
            435                  440                  445

Met Pro Thr Leu Cys  Arg
        450
```

NUCLEIC ACID ENCODING PP60$^{PIK}$ AND THE METHODS OF MAKING PP60$^{PIK}$

BACKGROUND OF THE INVENTION

This invention was made with government support under National Institute of Health Award Number DK 43808. Accordingly, the government retains certain rights in the invention.

The invention relates to insulin metabolism and more specifically to pp60$^{PIK}$, a protein which mediates insulin regulation of 3'-phosphatidyl-inositol (PI-3) kinase, and to the gene that encodes pp60$^{PIK}$.

SUMMARY OF THE INVENTION

In general, the invention features, a substantially pure nucleic acid, e.g., a DNA, which includes a sequence encoding a peptide having pp60$^{PIK}$ activity. In preferred embodiments: the sequence is at least 50%, more preferably at least 60%, yet more preferably at least 70%, and most preferably at least 80, 90, 95, or 99% homologous with the sequence from SEQ ID NO:1.

In another aspect, the invention features, a substantially pure nucleic acid, e.g., a DNA, which includes a nucleic acid sequence which hybridizes under high or low stringency to a nucleic acid which encodes a peptide with the same, or essentially the same, amino acid sequence as the peptide of SEQ ID NO:1.

In another aspect, the invention features, a substantially pure nucleic acid which includes a sequence encoding a peptide of 20 or more amino acids in length, the peptide having at least 90% homology with an amino acid sequence which is the same, or essentially the same, as the amino acid sequence of SEQ ID NO:1.

In another aspect, the invention includes a vector which includes a nucleic acid of the invention, preferably a substantially pure DNA of the invention, which encodes a peptide of the invention.

The invention also includes: a cell containing a nucleic acid of the invention; a cell which is capable of expressing a peptide of the invention; an essentially homogeneous population of cells, each of which includes a nucleic acid of the invention; and a method for manufacture of a peptide of the invention including culturing a cell which includes a nucleic acid of the invention in a medium to express the peptide.

In another aspect, the invention features a pp60$^{PIK}$ peptide of the invention, preferably a purified peptide of the invention, e.g.: a peptide having pp60$^{PIK}$ activity; a peptide encoded by a nucleic acid which hybridizes under high or low stringency conditions to a nucleic acid which encodes a peptide sequence which is the same, or essentially the same, as the amino acid sequence of SEQ ID NO1; a peptide of essentially of the same sequence as the amino acid sequence described in SEQ ID NO:1; a peptide of at least 20, preferably at least 30, more preferably at least 40, more preferably at least 50, and most preferably at least 60, amino acid residues in length; and, a peptide having at least 50%, more preferably at least 60%, yet more preferably at least 70%, yet more preferably at least 80%, and most preferably at least 90 or 99% homology with an amino acid sequence which is the same, or essentially the same, as the amino acid sequence of SEQ ID NO:1. In preferred embodiments the peptide is a recombinant peptide, e.g., a protein expressed from a nucleic acid of the invention.

In other aspects, the invention features: a therapeutic composition which includes a peptide of the invention and a pharmaceutically acceptable carrier; and, a therapeutic composition which includes a substantially pure nucleic acid of the invention and a pharmaceutically acceptable carrier.

In another aspect, the invention features a transgenic animal, e.g., a transgenic mammal, e.g., a mouse, having a transgene which includes an pp60$^{PIK}$ encoding DNA. In preferred embodiments the pp60$^{PIK}$ gene or DNA includes a mutation, e.g., a mutation that results in misexpression of pp60$^{PIK}$. In preferred embodiments the animal includes a second transgene, e.g., a transgene which includes the IRS-1 gene, e.g., an IRS-1 knockout.

In another aspect, the invention features a method of determining if a subject, e.g., a mammal, e.g., a human, is at risk for a disorder, e.g., an insulin-related disease, e.g., an insulin resistant insulin-related disease, e.g., Type II diabetes by evaluating an aspect of pp60$^{PIK}$ metabolism.

The method includes:

determining an aspect of pp60$^{PIK}$ metabolism in the subject, an abnormal level of pp60$^{PIK}$ metabolism being predictive of risk for the disorder.

The aspect of pp60$^{PIK}$ metabolism determined can include: the amount, distribution or structure of intracellular or extracellular pp60$^{PIK}$; the level of phosphorylation of pp60$^{PIK}$; the level of kinase activity of pp60$^{PIK}$; or the amount, distribution, or structure of pp60$^{PIK}$ encoding RNA.

In another aspect, the invention features a method of determining if a subject, e.g., a mammal, e.g., a human, is at risk for a disorder, e.g., an insulin-related disease, e.g., an insulin resistant insulin-related disease, e.g., Type II diabetes, by determining the structure of the pp60$^{PIK}$ gene.

The method includes:

determining if the structure of an allele of the pp60$^{PIK}$ gene in the subject differs from wild type, an other than wild type structure being predictive of risk for the disorder.

The structure of the pp60$^{PIK}$ gene can be determined, e.g., by hybridization based methods, e.g., by Southern analysis, or by DNA sequencing. Gross abnormalities, e.g., deletions, inversions, or translocations, or point mutations, can be predictive of risk. The method can be used to predict risk in the individual tested or in the individual's offspring. The method can be performed prenatally.

The invention also provides for a system to evaluate or screen treatments for their usefulness in the treatment a disorder, e.g., an insulin related disease, e.g., an insulin resistant disease, e.g., Type II diabetes. Accordingly, in another aspect, the invention includes a method of evaluating a treatment for use in treating a disorder. The method includes administering a treatment, e.g., administering compounds to a cultured cell or a test organism e.g., a mammal, and determining the effect of the agent on an aspect of pp60$^{PIK}$ metabolism. A change in an aspect of pp60$^{PIK}$ metabolism indicates an effect of the agent. In preferred embodiments the insulin related disease is an insulin resistant disease and the change in an aspect of metabolism is a change in the response to blood glucose levels.

Transgenic cells and animals of the invention also provide for a system to evaluate or screen treatments for their usefulness in the treatment a disorder, e.g., an insulin related disorder, e.g., an insulin-resistant disease, e.g., type II diabetes. Accordingly, the invention includes a method of evaluating an effect of a treatment, e.g., a therapeutic agent, on insulin metabolism in a transgenic cell or a transgenic animal having a pp60$^{PIK}$ transgene. The method includes:

administering a treatment to a transgenic cell or animal having a transgene which includes pp60$^{PIK}$, e.g., a cell or animal heterozygous or homozygous for a pp60$^{PIK}$ knockout; and determining the effect of the therapeutic agent on an aspect of insulin or pp60$^{PIK}$ metabolism. A change in the determined parameter being indicative of the usefulness or therapeutic value of the treatment. E.g., restoration of an aspect of insulin metabolism impaired by a misexpressed pp60$^{PIK}$, gene is indicative of the effectiveness of a treatment.

The invention also includes a method of assaying an effect of a therapeutic agent which mimics a first effect of insulin (the first effect mediated by pp60$^{PIK}$) without mimicking a second effect of insulin. The method includes: administering the agent to a cell grown in culture or to a test organism, e.g., a mammal; evaluating the agent's ability to mimic the first, pp60$^{PIK}$-mediated effect of insulin; and evaluating the agent's ability to mimic the second effect of insulin. In preferred embodiments evaluating the agent's ability to mimic the first, pp60$^{PIK}$-mediated effect of insulin includes: measuring a change in an aspect of pp60$^{PIK}$ metabolism, e.g., the level of pp60$^{PIK}$ expression, the kinase activity of pp60$^{PIK}$, the cellular or intra-cellular distribution of pp60$^{PIK}$, or the level of the pp60$^{PIK}$ phosphorylation.

The invention also features a method of treating a subject, e.g., a mammal e.g., a human, suffering from a disease caused by an abnormality of pp60$^{PIK}$ metabolism, e.g., a disease characterized by lower than desirable levels of pp60$^{PIK}$ activity. The method includes administering to the subject, a therapeutically effective amount of an agent, e.g., pp60$^{PIK}$, which alters an aspect of insulin metabolism, e.g., the level of PI 3' kinase phosphorylation.

The invention also features a method of treating a subject, e.g., a mammal, e.g., a human, suffering from a disease caused by unwanted tyrosine kinase activity. The method includes administering to the subject a therapeutically effective amount of a therapeutic agent, e.g., pp60$^{PIK}$ antagonist, e.g., a pp60$^{PIK}$ peptide which is an antagonist of pp60$^{PIK}$ mediated phosphorylation of a kinase, e.g., PI 3' kinase, a pp60$^{PIK}$ antisense molecule, or an anti-pp60$^{PIK}$ mAb, which modifies the ability of pp60$^{PIK}$ to alter the phosphorylation of the tyrosine kinase, thereby altering the tyrosine kinase activity. In preferred embodiments the tyrosine kinase activity results from a product of an oncogene.

The invention also features a method of treating a mammal, e.g., a human, suffering from a disease characterized by abnormal cell proliferation. The method includes administering to said mammal a therapeutically effective amount of a therapeutic agent, e.g., a pp60$^{PIK}$ antagonist, e.g., a pp60$^{PIK}$ peptide which is an antagonist of pp60$^{PIK}$ mediated phosphorylation of a kinase, e.g., PI 3' kinase, a pp60$^{PIK}$ antisense molecule, or an anti-pp60$^{PIK}$ mAb, which alters an aspect of pp60$^{PIK}$ metabolism. In preferred embodiments the aspect of pp60$^{PIK}$ metabolism is PI 3' kinase phosphorylation.

Methods of the invention can be used to diagnose the presence of diseases characterized by an abnormality in the structure or metabolism of pp60$^{PIK}$. The invention allows for the analysis of various aspects of insulin metabolism, e.g., for the detection of insulin-stimulated PI 3' kinase phosphorylation. The invention also provides useful tools for the testing and development of therapeutic agents used to treat insulin or pp60$^{PIK}$ related diseases.

The invention also features a method of evaluating an effect of a therapeutic agent which alters the ability of a tyrosine kinase to phosphorylate a substrate which includes the amino acid sequence YFIN (SEQ ID NO:3). The method includes administering the agent to a cultured cell or test organism, e.g., a mammal, and measuring the level of phosphorylation of a substrate which includes the amino acid sequence YFIN (SEQ ID NO:3), e.g., a naturally occurring YFIN-containing substrate of a tyrosine kinase or a YFIN-containing synthetic substrate.

The invention also includes a method of treating a mammal e.g., a human, suffering from a disease, disorder, or condition caused or characterized by the phosphorylation of a substrate of a tyrosine kinase, the substrate including the amino acid sequence YFIN (SEQ ID NO:3). The tyrosine kinase may be, e.g., a receptor tyrosine kinase, e.g., insulin receptor, epidermal growth factor (EGF) receptor, platelet derived growth factor, (PDGF) receptor, or insulin-like grog factor (ILG) receptor, or an oncogene product, e.g., the src, abl, or fms gene product. The method includes administering a therapeutically effective amount of a therapeutic agent, e.g., a peptide which includes the sequence YFIN (SEQ ID NO: 3) e.g., pp60$^{PIK}$ or a fragment thereof which includes the amino acid sequence YFIN (SEQ ID NO: 3), mimetic or a YFIN-continuing peptide.

In another aspect, the invention includes peptides capable of inhibiting an interaction, preferably a site specific interaction, of an SH2-domain-containing protein, e.g., a signal transduction protein, e.g., a cytoplasmic or a transmembrane signal transduction protein, a receptor protein, e.g., the insulin receptor or the PDGF receptor, or a protein which is active in the regulation of cell proliferation, e.g., an oncogene product, with a second protein containing the sequence YFIN (SEQ ID NO:3), a protein capable of altering the state of phosphorylation of a tyrosine residue, e.g., a tyrosine kinase, e.g., pp60$^{PIK}$. Peptides of the invention include the sequence R$^1$FIN(SEQ IS NO:4) (wherein R$^1$ is tyrosine, phosphotyrosine, or more preferably, an analog of phosphotyrosine having a hydrolysis resistant phosphorous moiety). The invention also includes mimetics of these peptides.

In another aspect, the invention features a method of inhibiting an interaction, preferably a site specific interaction, between a first molecule which includes an SH2 domain, e.g., a signal transduction protein, e.g., a cytoplasmic or a transmembrane signal transduction protein, a receptor protein, e.g., the insulin receptor or the PDGF receptor, or a protein which is active in the regulation of cell proliferation, e.g., an oncogene product, and a second molecule, e.g., a protein containing the sequence YFIN (SEQ ID NO:3) a protein capable of altering the state of phosphorylation of a tyrosine residue, e.g., a tyrosine kinase, e.g., pp60$^{PIK}$. The method includes contacting the first molecule with an inhibitor molecule which includes a peptide of the invention or which includes a mimetic of a peptide of the invention.

In another aspect, the invention features a method of treating a mammal, e.g., a human, having a condition characterized by unwanted cell proliferation including administering to the mammal an amount of a YFIN-containing peptide of the invention, or a mimetic of a peptide of the invention, sufficient to prevent or inhibit the unwanted cell proliferation.

The invention also includes methods of increasing the affinity of a YFIN-containing phosphopeptide for its substrate, e.g., a protein, containing a SH2-domain. The method includes replacing the phosphotyrosine of the YFIN (SEQ ID NO:3) motif with a moiety which is more electronegative than the phosphate moiety of phosphotyrosine such as in R$^1$—OPO$_3$H$_2$ where R$^1$ can be CHF, CF$_2$, CHCl, CCl$_2$, or CClF.

Methods of the invention allow the treatment of a variety of diseases, e.g., insulin related diseases, insulin resistant diseases, diseases characterized by abnormal cellular proliferation, and diseases caused by the phosphorylation of a substrate by a tyrosine kinase, by intervening in aspects of pp60$^{PIK}$ metabolism.

Other features and advantages of the invention will be apparent from the following description of the preferred embodiments and from the claims.

DETAILED DESCRIPTION

The drawings are first briefly described.

Drawings FIG. 1 is a diagram of the DNA sequence of a pp60$^{PIK}$ cDNA (SEQ ID NO:1) and the amino acid sequence of pp60$^{PIK}$ (SEQ ID NO:1 and 2).

FIG. 4 is a diagram of the amino acid sequences of pp60$^{PIK}$, p85α and p85β, which shows the homologous regions among the three proteins.

Figure 5A:
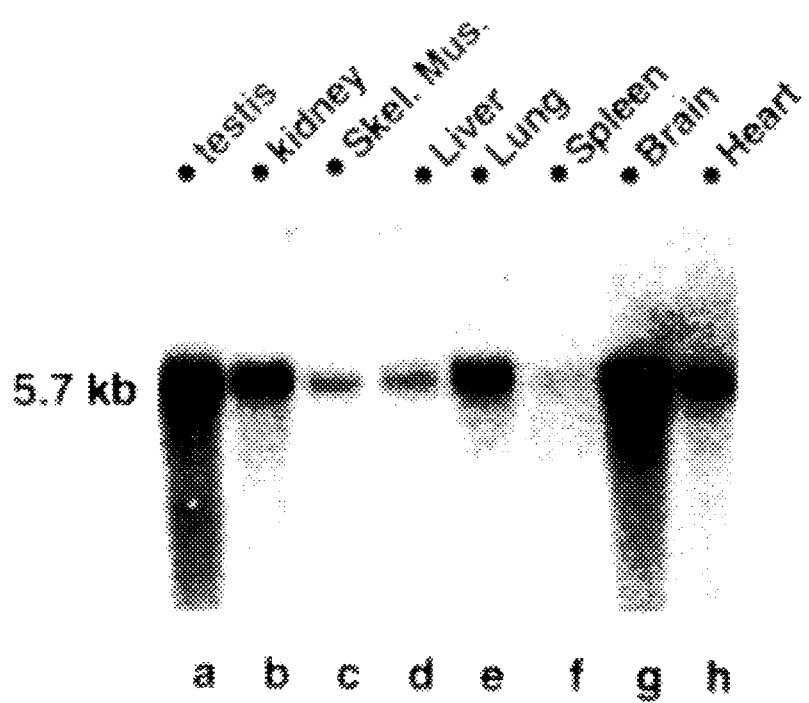
Figure 5B:
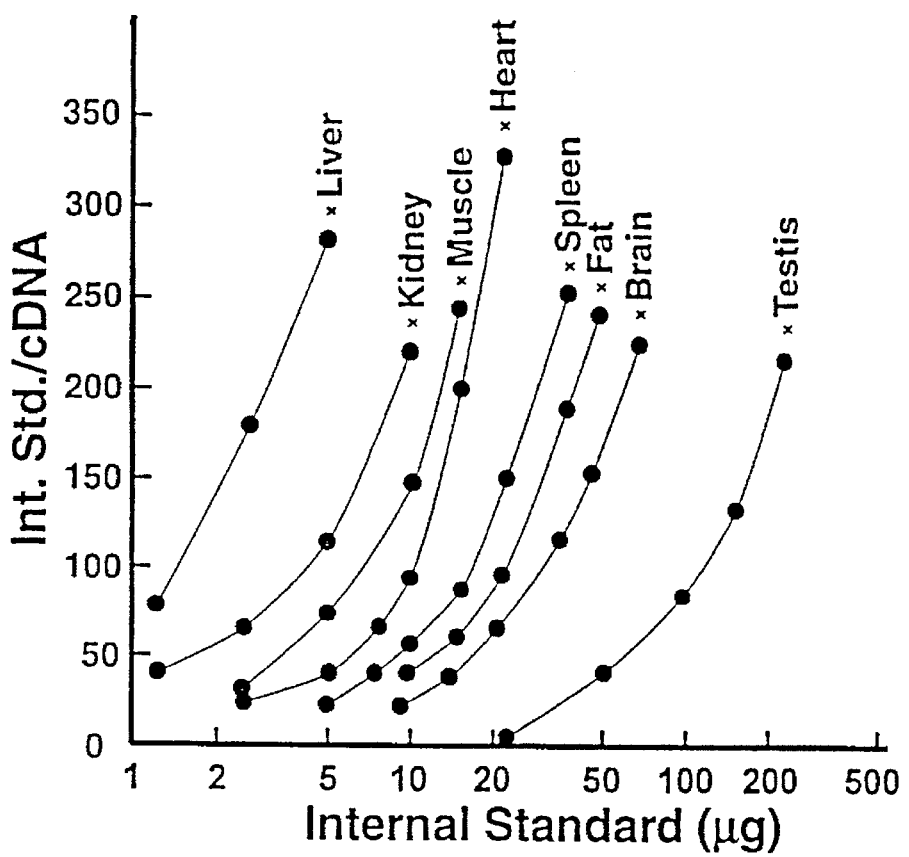
Figure 5C:
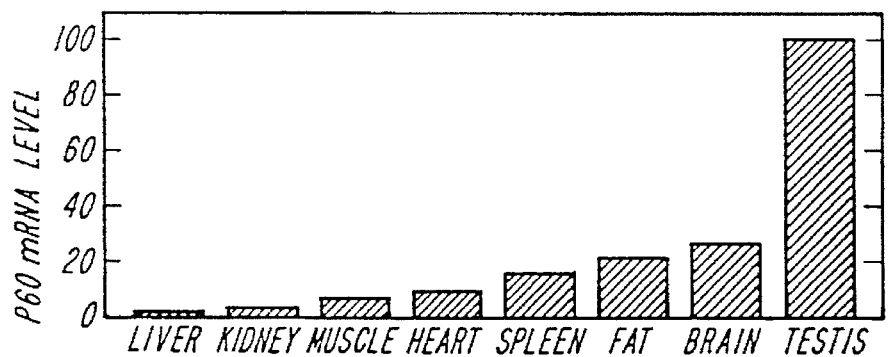

FIG. 5 is a depiction, of the results of experiments performed to determine the distribution of pp60$^{PIK}$ in a variety of mouse tissues. A, hybridization analysis; B, competitive PCR experiments; C, relative levels in various tissues.

Figure 6A:
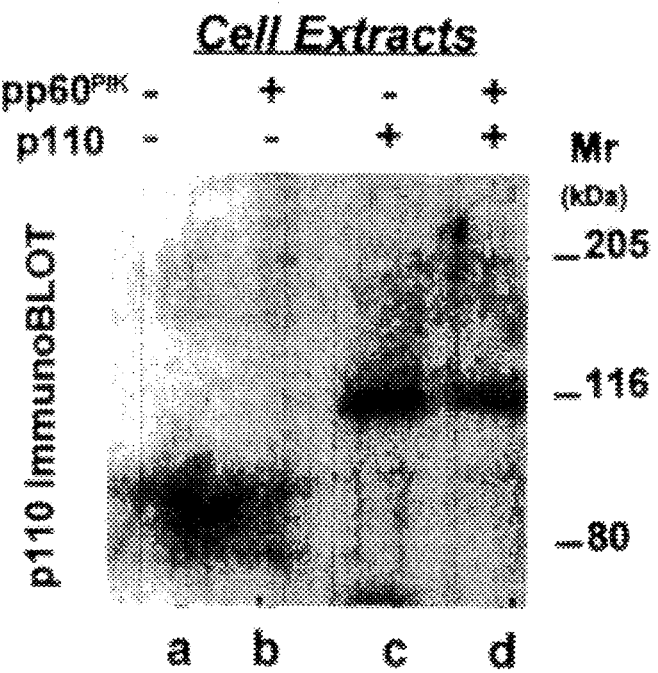
Figure 6B:
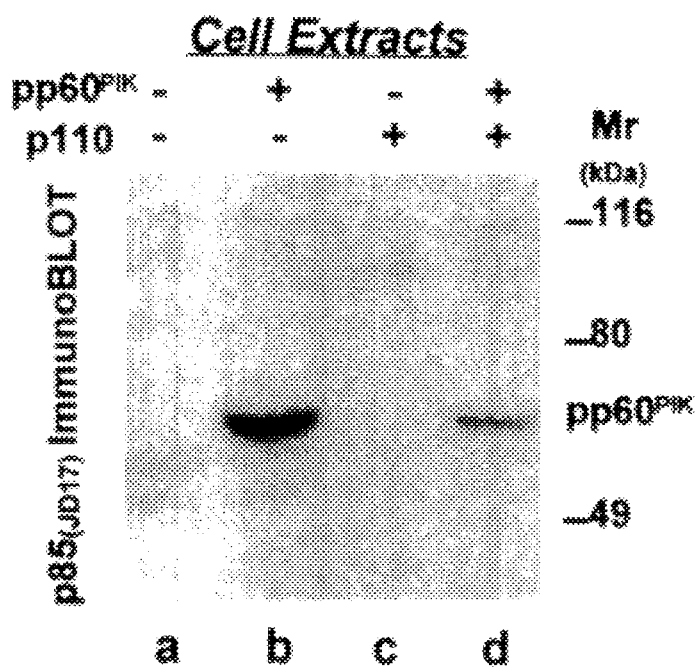

FIG. 6 is a depiction(Left panel: p110 immunoblot; Right panel: p85 immunoblot) of the results of experiments performed to determine the expression of p110 and pp60$^{PIK}$ in insect Sf-9 cells.

Figure 7:
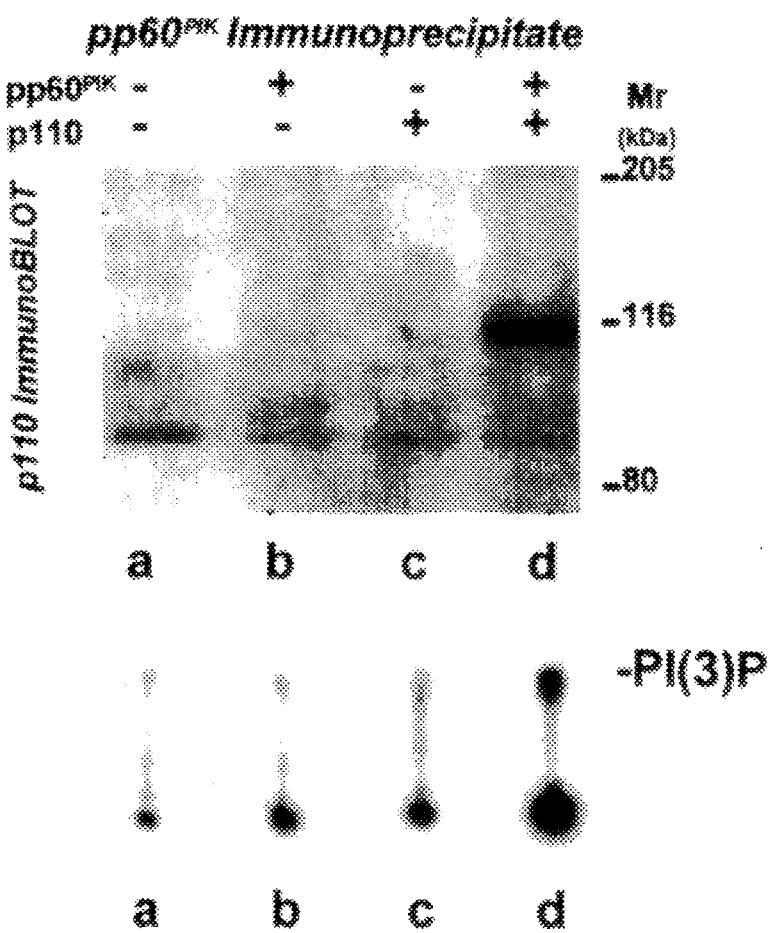

FIG. 7 is a depiction of the results of experiments performed to determine the association of p110 and pp60$^{PIK}$ in insect Sf-9 cells.

Figures 8A, 8B, 8C:
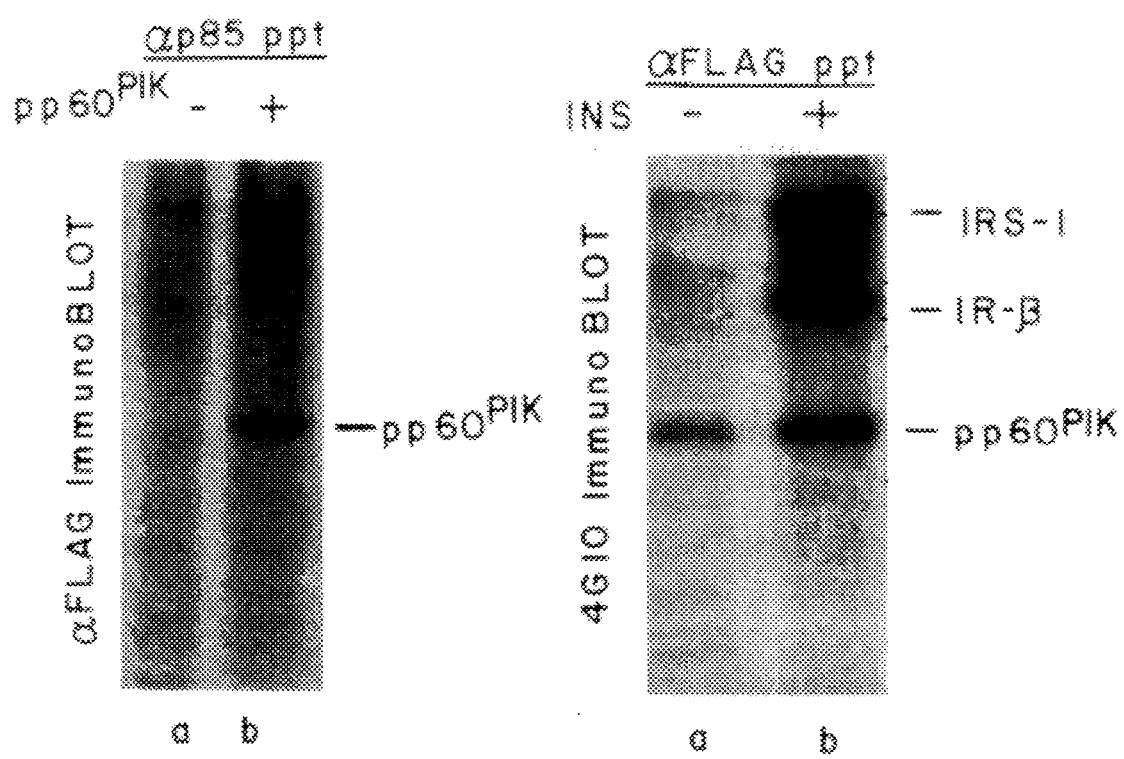

FIG. 8 is a depiction of the results of experiments performed to determine the expression of pp60$^{PIK}$ in CHO cells. Left, anti-p85 preciptiation; Center, anti-FLAG precipitation; Right, anti-IRS-1 precipitation.

Figure 9A:
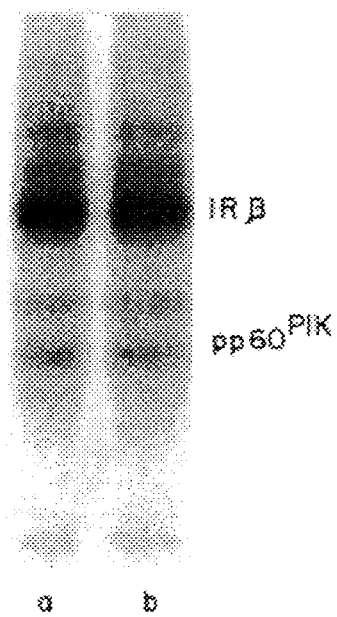
Figure 9B:

FIG. 9 is a depiction of the results of experiments performed to show phosphorylation of pp60$^{PIK}$ by the insulin receptor.

Figure 10B:
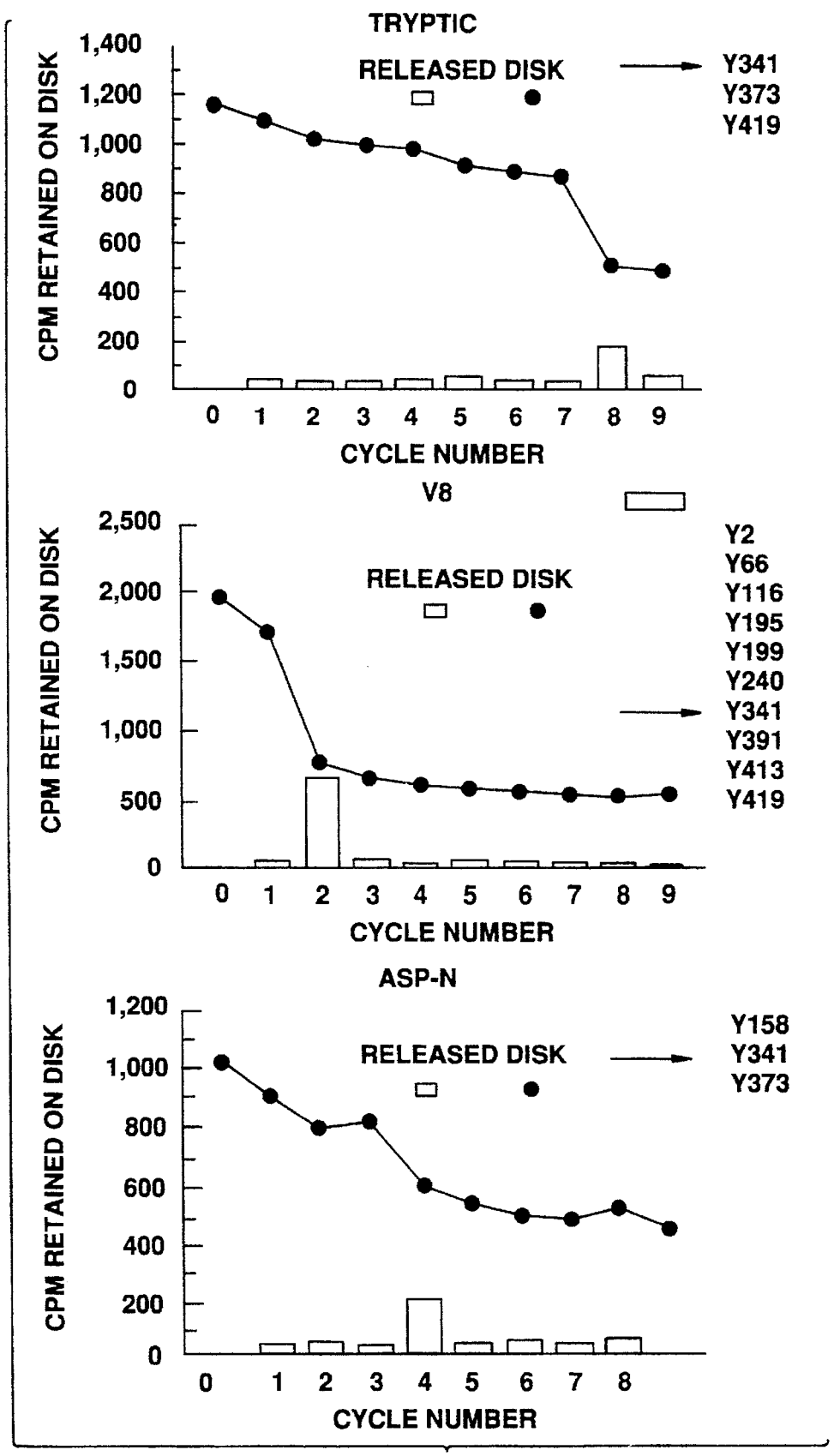

FIG. 10 is a depiction of the results of experiments performed to identify the tyrosine phosphorylation site (SEQ ID NO:6–24) in pp60$^{PIK}$.

Figure 11:
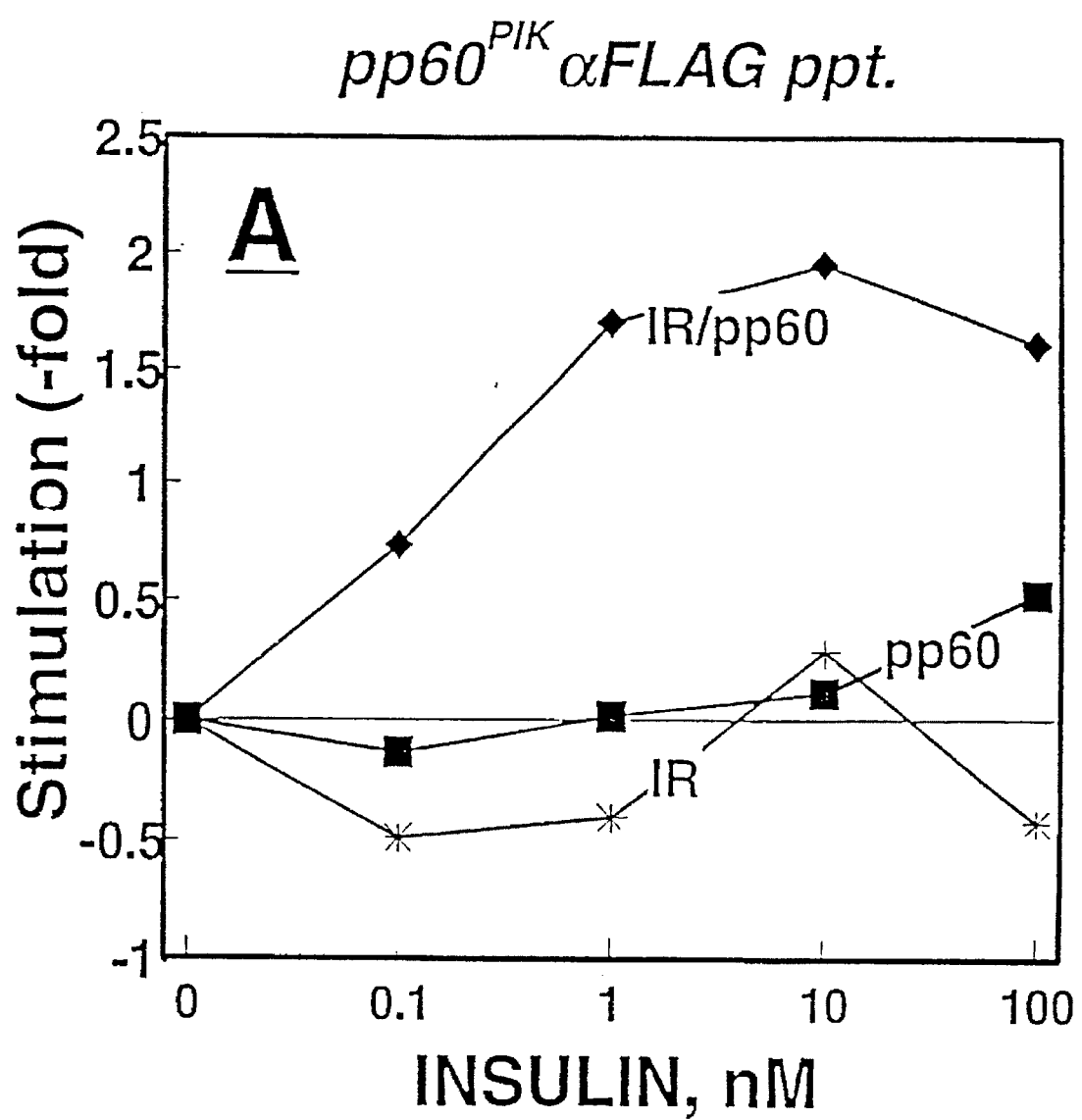

FIG. 11 is a depiction of the results of experiments performed to determine the effect of insulin on PI 3'-kinase activity on mammalian cells (Chinese hamster ovary cells) overexpressing pp60$^{PIK}$.

pp60$^{PIK}$

In general, the invention features, a substantially pure nucleic acid, e.g., a DNA, which includes (or consists essentially of) a nucleic acid sequence encoding pp60$^{PIK}$, or a pp60$^{PIK}$ peptide. In preferred embodiments: the encoded peptide has pp60$^{PIK}$ activity; the nucleic acid sequence is at least 50%, more preferably at least 60%, yet more preferably at least 70%, and most preferably at least 80, 90, 95, or 99%, homologous with DNA from SEQ ID NO:1; the encoded amino acid sequence is such that it can be encoded by a nucleic acid which hybridizes under high or low stringency conditions to a nucleic acid which encodes a peptide with the same, or essentially the same, amino acid sequence as the peptide of SEQ ID NO:1; the pp60$^{PIK}$ peptide is at least 30, more preferably at least 40, more preferably at least 50, and most preferably at least 60, 80, 100, or 120 amino acid residues in length; the pp60$^{PIK}$ peptide is at least 50%, more preferably at least 60%, more preferably at least 70%, yet more preferably at least 80%, and most preferably at least 90 or 99% homologous with an amino acid sequence which is the same, or essentially the same, as the peptide sequence of SEQ ID NO:1 and, the amino acid sequence of the pp60$^{PIK}$ peptide is essentially the same as the peptide sequence, or a fragment of the sequence, described in SEQ ID NO:1.

In preferred embodiments the encoded peptide has one or more of the following properties: it can bind to IRS-1; it can bind to the PI 3'-kinase 110 Kd catalytic subunit; it does not contain an SH3 domain; it can be phosphorylated by the insulin receptor or other tyrosine kinases; it does not contain a BCR-homology region (such as is found in p85s); it contains one and preferably two, SH2 domains; it contains one tyrosine phosphorylation site.

In another aspect, the invention features, a substantially pure nucleic acid, e.g., DNA, which includes (or consists essentially of) a nucleic acid sequence which hybridizes under high or low stringency to a nucleic acid which encodes a peptide with the same, or essentially the same, amino acid sequence as the peptide of SEQ ID NO:1. In preferred embodiments: the DNA sequence is at least 50%, more preferably at least 60%, yet more preferably at least 70%, and most preferably at least 80, 90, 95, or 99% homologous with DNA from of SEQ ID NO1; the substantially pure DNA encodes a peptide at least 30, more preferably at least 40, more preferably at least 50, and most preferably at least 60, 80, 100, or 120 amino acid residues in length; the substantially pure DNA encodes a peptide at least 50%, more preferably at least 60%, yet more preferably at least 70%, and most preferably at least 90 or 99% homologous with an amino acid sequence which is the same, or essentially the same, as the amino acid sequence of SEQ ID NO:1; and, the substantially pure DNA encodes a peptide having essentially the same amino acid sequence, or a fragment of the amino acid sequence, described in SEQ ID NO:1.

In preferred embodiments the encoded peptide has one or more of the following properties: it can bind to IRS-1; it can bind to the PI 3'-kinase 110 Kd catalytic subunit; it does not contain an SH3 domain; it can be phosphorylated by the insulin receptor or other tyrosine kinases; it does not contain a BCR-homology region (such as is found in p85s); it contains one and preferably two, SH2 domains; it contains one tyrosine phosphorylation site.

In another aspect, the invention features, a substantially pure nucleic acid, e.g., a DNA, which includes (or consists essentially of) a sequence encoding a peptide of 20 or more amino acids in length, the peptide having at least 90% homology with an amino acid sequence which is the same, or essentially the same, as the amino acid sequence of SEQ ID NO:1. In preferred embodiments the substantially pure nucleic acid encodes: a peptide which is at least 30, more preferably at least 40, more preferably at least 50, and most preferably at least 60, amino acid residues in length; a peptide which is at least 50%, more preferably at least 60%, yet more preferably at least 70%, yet more preferably at least 80%, and most preferably at least 90 or 99% homologous with an amino acid sequence which is the same, or essentially the same, as the amino acid sequence of SEQ ID NO:1; and, a peptide with pp60$^{PIK}$ activity.

In preferred embodiments the encoded peptide has one or more of the following properties: it can bind to IRS-1; it can bind to the PI 3'-kinase 110 Kd catalytic subunit; it does not contain an SH3 domain; it can be phosphorylated by the insulin receptor or other tyrosine kinases; it does not contain a BCR-homology region (such as is found in p85s); it contains one and preferably two, SH2 domains; it contains one tyrosine phosphorylation site.

In another aspect, the invention includes a vector which includes nucleic acid, e.g., a DNA, of the invention, preferably a substantially pure nucleic acid of the invention, which encodes a peptide of the invention, e.g.: DNA which includes a sequence encoding a peptide having pp60$^{PIK}$ activity; DNA which hybridizes under high or low stringency conditions to a nucleic acid which encodes a peptide with the same, or essentially the same, amino acid sequence of SEQ ID NO:1; DNA which encodes a peptide of essentially the sequence described in SEQ ID NO:1; DNA which includes a sequence encoding a peptide of at least 20, preferably at least 30, more preferably at least 40, more preferably at least 50, and most preferably at least 60, amino acid residues in length; and DNA which encodes a peptide at least 50%, more preferably at least 60%, yet more preferably at least 70%, yet more preferably at least 80%, and most preferably at least 90 or 99% homologous with an amino acid sequence which is the same, or essentially the same, as the amino acid sequence of SEQ ID NO:1. Other preferred embodiments include those in which: the DNA sequence is at least 85%, more preferably at least 90%, yet more preferably at least 95%, and most preferably at least 98 or 99% homologous with the DNA sequence of SEQ ID NO:1.

The invention also includes: a cell containing a nucleic acid, e.g., a DNA, preferably a substantially pure nucleic acid, of the invention, preferably, a cell which is capable of expressing a peptide of the invention; an essentially homogeneous population of cells, each of which includes a sequence, preferably a substantially pure nucleic acid, of the invention, and a method for manufacture of a peptide of the invention including culturing a cell which includes a nucleic acid, preferably a substantially pure nucleic acid of the invention in a medium to express the peptide.

In another aspect, the invention features a peptide of the invention, preferably a purified peptide of the invention, e.g.: a peptide having pp60$^{PIK}$ activity; a peptide encoded by a DNA which hybridizes under high or low stringency conditions to a nucleic acid which encodes peptide sequence which is the same, or essentially the same, as the amino acid sequence of SEQ ID NO:1; a peptide of essentially the sequence described in SEQ ID NO:1; a peptide of at least 20, preferably at least 30, more preferably at least 40, more preferably at least 50, and most preferably at least 60, amino acid residues in length; and, a peptide having at least 50%, more preferably 60%, yet more preferably 70%, yet more preferably 80%, and most preferably at least 90 or 99% homology with an amino acid sequence which is the same, or essentially the same, as the amino acid sequence of SEQ ID NO:1.

In preferred embodiments the peptide has one or more of the following properties: it can bind to IRS-1; it can bind to the PI 3'-kinase 110 Kd catalytic subunit; it does not contain an SH3 domain; it can be phosphorylated by the insulin receptor or other tyrosine kinases; it does not contain a BCR-homology region (such as is found in p85s); it contains one and preferably two, SH2 domains; it contains one tyrosine phosphorylation site.

In another aspect, the invention features a peptide of the invention, preferably a purified peptide of the invention, produced by expression of a nucleic acid of the invention, preferably a substantially pure nucleic acid of the invention, e.g.: a peptide produced by the expression of: a purified DNA encoding a peptide having pp60$^{PIK}$ activity; a peptide expressed from DNA which hybridizes under high or low stringency conditions to a nucleic acid which encodes a peptide with the same, or essentially the same, amino acid sequence as the peptide of SEQ ID NO:1; a peptide expressed from DNA which encodes a peptide of essentially the sequence described in SEQ ID NO:1; a peptide expressed from a purified DNA which includes a sequence encoding a peptide of at least 20, preferably at least 30, more preferably at least 40, more preferably at least 50, and most preferably at least 60, amino acid residues in length; and a peptide expressed from DNA having at least 50%, more preferably 60%, yet more preferably 70%, yet more preferably 80%, and most preferably at least 90 or 99% homology with an amino acid sequence which is the same, or essentially the same, as the sequence of SEQ ID NO:1.

In preferred embodiments the encoded peptide has one or more of the following properties: it can bind to IRS-1; it can bind to the PI 3'-kinase 110 Kd catalytic subunit; it does not contain an SH3 domain; it can be phosphorylated by the insulin receptor or other tyrosine kinases; it does not contain a BCR-homology region (such as is found in p85s); it contains one and preferably two, SH2 domains; it contains one tyrosine phosphorylation site.

In another aspect, the invention features: a therapeutic composition which includes a peptide of the invention and a pharmaceutically acceptable carrier; and, a therapeutic composition which includes a purified DNA of the invention and a pharmaceutically acceptable carrier In another aspect, the invention features a transgenic animal, e.g., a transgenic mammal, e.g., a mouse, having a transgene which includes a pp60$^{PIK}$ encoding DNA. In preferred embodiments the pp60$^{PIK}$ gene or DNA includes a mutation, e.g., a mutation that results in misexpression of pp60$^{PIK}$. In other preferred embodiments, the transgenic animal includes a second transgene, e.g., a transgene which includes the IRS-1 gene, e.g., an IRS-1 knockout.

In another aspect, the invention features a method of determining if a subject, e.g., a mammal, e.g., a human, is at risk for a disorder, e.g., an insulin-related disease, e.g., an insulin resistant insulin-related disease, e.g., Type II diabetes.

The method includes evaluating or measuring an aspect of pp60$^{PIK}$ metabolism in the subject, an abnormal level of pp60$^{PIK}$ metabolism being predictive of the disorder. Preferred embodiments include those in which: the evaluation or measurement includes determining the level of pp60$^{PIK}$; the evaluation or measurement includes determining the level of phosphorylation of the pp60$^{PIK}$; the evaluation or measurement includes determining the level of kinase activity of pp60$^{PIK}$; and the evaluation or measurement includes determining the amount of pp60$^{PIK}$ encoding RNA.

In another aspect, the invention features a method of determining if a subject, e.g., a mammal, e.g., a human, is at risk for a disorder, e.g., an insulin-related disease, e.g., an insulin resistant insulin-related disease, e.g., Type II diabetes, by determining the structure of the pp60$^{PIK}$ gene.

The method includes determining, preferably prenatally, if a subject, e.g., a mammal, e.g., a human, is at risk for a disorder, e.g., an insulin-related disease, e.g., an insulin resistant insulin-related disease, e.g., Type II diabetes, in a mammal, e.g., a human, by determining the structure of the gene which expresses pp60$^{PIK}$, an abnormal structure being predictive of risk.

The invention also provides for a system to evaluate or screen treatments of usefulness in the treatment of a disorder, e.g., an insulin-related disorder. Accordingly, in another aspect, the invention includes a method of evaluating a treatment for use in treating a disorder. The method includes administering the treatment to a cultured cell or a mammal, and measuring the effect of the treatment on an aspect of pp60$^{PIK}$ metabolism, e.g., measuring the level of pp60$^{PIK}$ expression, the cellular or intra-cellular distribution of pp60$^{PIK}$, or the level of the pp60$^{PIK}$ phosphorylation. A change in an aspect of pp60$^{PIK}$ metabolism indicates an effect of the treatment. In preferred embodiments the insulin-related disease is an insulin resistant disease and the change in an aspect of metabolism is a change in the response to blood glucose levels.

Transgenic cells and animals of the invention also provide for a system to evaluate or screen treatments of usefulness in the treatment a disorder, e.g., an insulin related disorder. Accordingly, the invention includes a method of evaluating an effect of a treatment, e.g., a therapeutic agent, on insulin metabolism in a transgenic cell or a transgenic animal having a pp60$^{PIK}$ transgene. The method includes administering a treatment to a transgenic cell or animal, e.g., a transgenic mammal, e.g., a mouse, having a transgene which includes pp60$^{PIK}$, and determining the effect of the therapeutic agent on an aspect of insulin metabolism. The aspect of insulin metabolism followed can include, e.g., measuring responsiveness to blood glucose levels or by the phosphorylation of PI 3' kinase in response to insulin administration. In preferred embodiments, the pp60$^{PIK}$ gene or DNA includes a mutation, e.g., a deletion or other mutation which results in misexpression of pp60$^{PIK}$. A change in the determined parameter for insulin metabolism being indicative of the usefulness of therapeutic value of the treatment, e.g., restoration of an aspect of insulin metabolism impaired by a misexpressed pp60$^{PIK}$ gene is indicative of the effectiveness of a treatment.

The invention also includes a method of assaying an effect of a therapeutic agent which mimics a first effect of insulin (the first effect mediated by pp60$^{PIK}$) without mimicking a second effect of insulin. The method includes: administering the agent to a cell grown in culture or to a test organism, e.g., a mammal; evaluating the agent's ability to mimic the first, pp60$^{PIK}$-mediated effect of insulin; and evaluating the agent's ability to mimic the second effect of insulin. In preferred embodiments evaluating the agent's ability to mimic the first, pp60$^{PIK}$-mediated effect of insulin includes: and measuring a change in an aspect of pp60$^{PIK}$ metabolism, e.g., the level of pp60$^{PIK}$ expression, the kinase activity of pp60$^{PIK}$, the cellular or intra-cellular distribution of pp60$^{PIK}$, or the level of the pp60$^{PIK}$ phosphorylation.

The invention also features a method of treating a subject, e.g., a mammal e.g., a human, suffering from a disease caused by an abnormality of pp60$^{PIK}$ metabolism, e.g., a disease characterizing lower than desirable levels of pp60$^{PIK}$ activity. The method includes administering to the subject, a therapeutically effective amount of an agent, e.g., pp60$^{PIK}$, which alters an aspect of insulin metabolism, e.g., the level of PI 3' kinase phosphorylation.

The invention also features a method of treating a subject, e.g., a mammal, e.g., a human, suffering from a disease caused by unwanted tyrosine kinase activity. The method includes administering to the subject a therapeutically effective amount of a therapeutic agent, e.g., pp60$^{PIK}$ antagonist, e.g., a pp60$^{PIK}$ peptide which is an antagonist of pp60$^{PIK}$ mediated phosphorylation of a kinase, e.g., PI 3' kinase, a pp60$^{PIK}$ antisense molecule, or an anti-pp60$^{PIK}$ mAb, which modifies the ability of pp60$^{PIK}$ to alter the phosphorylation of the tyrosine kinase, thereby altering the tyrosine kinase activity. In preferred embodiments the tyrosine kinase activity results from a product of an oncogene.

The invention also features a method of treating a mammal, e.g., a human, suffering from a disease characterized by abnormal cell proliferation. The method includes administering to said mammal a therapeutically effective amount of a therapeutic agent, e.g., a pp60$^{PIK}$ antagonist, e.g., a pp60$^{PIK}$ peptide which is an antagonist of pp60$^{PIK}$ mediated phosphorylation of a kinase, e.g., PI 3' kinase, a pp60$^{PIK}$ antisense molecule, or an anti-pp60$^{PIK}$ mAb, which alters an aspect of pp60$^{PIK}$ metabolism. In preferred embodiments the aspect of pp60$^{PIK}$ metabolism is PI 3' kinase phosphorylation.

The invention also features a method of evaluating an effect of a therapeutic agent which alters the ability of a tyrosine kinase to phosphorylate a substrate which includes the amino acid sequence YFIN (SEQ ID NO:3). The method includes administering the agent to a cultured cell or test organism, e.g., a mammal, and measuring the level of phosphorylation of a substrate which includes the amino acid sequence YFIN (SEQ ID NO:3) e.g., a naturally occurring YFIN-containing substrate of a tyrosine kinase or a YFIN-containing synthetic substrate. In preferred embodiments: the substrate is a peptide which includes the sequence YFIN (SEQ ID NO:3); the substrate is pp60$^{PIK}$ or a YFIN (SEQ ID NO:3) containing any fragment thereof. In preferred embodiments: the peptide or fragment is between 4 and 30 amino acids in length; the peptide or fragment is between 4 and 15 amino acids in length; the peptide or fragment is at least 40%, preferably at least 80%, and more preferably at least 95% homologous, with a segment of a naturally occurring protein, e.g., tyrosine phosphatase substrate, e.g., pp60$^{PIK}$, which interacts with an SH2 containing protein.

The invention also includes a method of treating a mammal e.g., a human, suffering from a disease, disorder, or condition caused or characterized by the phosphorylation of a substrate of a tyrosine kinase, the substrate including the amino acid sequence YFIN (SEQ ID NO:3). The tyrosine kinase may be, e.g., a receptor tyrosine kinase, e.g., insulin receptor, epidermal growth factor EGF) receptor, platelet derived growth factor, (PDGF) receptor, or insulin-like growth factor (ILG) receptor, or an oncogene product, e.g., the src, abl, or fms gene product. The method includes administering a therapeutically effective amount of a therapeutic agent, e.g., a peptide which includes the sequence YFIN (SEQ ID NO:3), e.g., pp60$^{PIK}$ or a fragment thereof which includes the amino acid sequence YFIN (SEQ ID NO:3), or a mimetic of a YFIN-containing peptide. In preferred embodiments the substance blocks phosphorylation of the naturally occurring substrate by competitive or non-competitive inhibition of the naturally occurring substrate. In preferred embodiments: the peptide or fragment is between 4 and 30 amino acids in length; the peptide or fragment is between 4 and 15 amino acids in length; the peptide or fragment is at least 40%, preferably at least 80%, and more preferably at least 95% homologous, with a segment of a naturally occurring protein, e.g., tyrosine phosphatase substrate, e.g., pp60$^{PIK}$, which interacts with an SH2 containing protein.

In another aspect, the invention includes peptides capable of inhibiting an interaction, preferably a site specific interaction, of an SH2-domain-containing protein, e.g., a signal transduction protein, e.g., a cytoplasmic or a transmembrane signal transduction protein, a receptor protein, e.g., the insulin receptor or the PDGF receptor, or a protein which is active in the regulation of cell proliferation, e.g., an oncogene product, with a second protein containing the sequence YFIN (SEQ ID NO:3) a protein capable of altering the state of phosphorylation of a tyrosine residue, e.g., a tyrosine kinase, e.g., pp60$^{PIK}$. Peptides of the invention include the sequence R$^1$FIN (SEQ ID NO: 4) (wherein R$_1$ is tyrosine, phosphotyrosine, or more preferably, an analog of phosphotyrosine having a hydrolysis resistant phosphorous moiety, e.g. phosphonomethylphenylalanine (Pmp), or a hydrolysis resistant phosphorous moiety which is more electronegative than the phosphate group of phosphotyrosine, for example, mono- or difluorophosphonomethylphenlalanine (FPmp or F$_2$Pmp, respectively). The invention also includes mimetics of these peptides.

In preferred embodiments: the peptide is between 4 and 30 amino acids in length; the peptide is between 4 and 15 amino acids in length; the peptide is at least 40%, preferably at least 80%, and more preferably at least 95% homologous, with a segment of a naturally occurring protein, e.g., tyrosine phosphatase substrate, e.g., pp60$^{PIK}$, which interacts with an SH2 containing protein.

In another aspect, the invention features a method of inhibiting an interaction, preferably a site specific interaction, between a first molecule which includes an SH2 domain, e.g., a signal transduction protein, e.g., a cytoplasmic or a transmembrane signal transduction protein, a receptor protein, e.g., the insulin receptor or the PDGF receptor, or a protein which is active in the regulation of cell proliferation, e.g., an oncogene product, and a second molecule, e.g., a protein containing the sequence YFIN (SEQ ID NO:3), a protein capable of altering the state of phosphorylation of a tyrosine residue, e.g., a tyrosine kinase, e.g., pp60$^{PIK}$. The method includes contacting the first molecule with an inhibitor molecule which includes a peptide of the invention or which includes a mimetic of a peptide of the invention.

Preferred embodiments include those in which: the first molecule is a molecule which transmits a signal, e.g., an extracellular signal, across a membrane and the second molecule is an enzyme which can alter the phosphorylation state of tyrosine, e.g., a tyrosine kinase; the first molecule is an oncogene protein and the second molecule is an enzyme which can alter the phosphorylation state of tyrosine, e.g., a tyrosine kinase, e.g., pp60$^{PIK}$; the first molecule is the insulin receptor and the second molecule is an enzyme which can alter the phosphorylation state of tyrosine, e.g., a tyrosine kinase; the inhibitor molecule inhibits the first molecule from binding to the second molecule; the inhibitor molecule inhibits the phosphorylation of the first molecule; the inhibitor inhibits the binding of the first molecule to a third molecule; the inhibitor results in an alteration of a catalytic activity of the first molecule, e.g., the inhibitor alters the ability of the first molecule to alter the phosphorylation state of itself or another molecule.

In another aspect, the invention features a method of treating a mammal, e.g., a human, having a condition characterized by unwanted cell proliferation including administering to the mammal an amount of a YFIN-containing peptide of the invention, or a mimetic of a peptide of the invention, sufficient to prevent or inhibit the unwanted cell proliferation. In a preferred embodiment the peptide prevents the association of an SH2 domain containing oncogene with a second molecule, e.g., a protein containing the sequence YFIN (SEQ ID NO:3), e.g., a protein capable of altering the state of phosphorylation of a tyrosine residue, e.g., a tyrosine kinase.

The invention also includes methods of increasing the affinity of a YFIN-containing phosphopeptide for its substrate, e.g., a protein containing a SH2-domain. The method includes replacing the phosphotyrosine of the YFIN (SEQ ID NO:3) motif with a moiety which is more electronegative than the phosphate moiety of phosphotyrosine such as in R$^1$—OPO$_3$H$_2$ where R$^1$ can be CHF, CF$_2$, CHCl, CCl$_2$, or CClF.

The invention includes peptides which have been modified to make them more resistant to proteolytic degradation and include e.g., depsipeptide derivatives of the peptides disclosed herein, e.g., peptides which have been modified by the reduction of amide bonds, the inclusion of D-amino acids, or end methylation.

An interaction between an SH2 domain containing protein and a second molecule e.g., a protein, as used herein, refers to any of: binding characterized by noncovalent or covalent interactions; an interaction which includes the alteration of the phosphorylation state of either the SH2 domain containing or another molecule, e.g., the second molecule; or to an interaction which includes an alteration of a catalytic ability of the SH2 domain containing proteins, or another molecule, e.g., the second molecule.

Analog of phosphotyrosine having a hydrolysis resistant phosphorous moiety, as used herein, refers to an amino acid with a side chain having a moiety of the formula

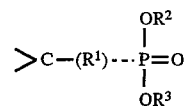

wherein R$^1$ is a moiety which renders the phosphate group more resistant to enzymatic hydrolysis than would be the case if the R$^1$ was O. R$^2$ and R$^3$ are preferably H. A preferred example of R$^1$ is CR$^4$R$^5$, wherein R$^4$ is H, or a small electronegative atom, e.g., F or Cl, and R$^5$ is H or a small electronegative atom, e.g., F or Cl. Particularly preferred embodiments of the invention include hydrolysis resistant phosphorous moieties that are more electronegative than the phosphate moiety of phosphotyrosine, for example, where R$^1$ is —CHF, —CF$_2$, —CClF, —CHCl, or CCl$_2$. Increasing the electronegativity of the phosphate moiety in an analog of phosphotyrosine increases the binding affinity of peptides containing the analog to a substrate such as protein containing an SH$_2$ domain. In some cases, the affinity can exceed that of peptides containing phosphotyrosine.

SH2 domain containing proteins are involved in cellular signaling, e.g., in the signal transduction mediated by insulin and the insulin receptor and by several classes of oncogenes. The invention provides for inhibitors of these cellular signal transduction systems by inhibiting an interaction between the SH2 domain of the signal transduction protein and a YFIN motif present on another protein. In the case of oncogenes, the invention provides for interference with the transduction of growth signals and thereby allows for control of unwanted cellular proliferation.

The invention also provides peptide inhibitors of PTPases. The peptide inhibitors, or analogs, which may or may not have homology with naturally occurring protein tyrosine phosphatase substrates, include an analog of phosphotyrosine having a hydrolysis resistant phosphorous moiety, e.g., phosphonomethylphenylalanine or a hydrolysis resistant phosphorous moiety which is more electronegative than the phosphate group of phosphotyrosine, for example, FPmp or F$_2$Pmp. The phosphotyrosine analog includes a phenyl group substituted with an —O—PO$_3$H$_2$ analog, e.g., —R—PO$_3$H$_2$, where R can be any group which confers greater resistance to hydrolysis than does —O—, e.g, CR$^4$R$^5$ wherein R$^4$ can be H, F or Cl and R$^5$ can be H, F or Cl. Preferred phosphotyrosine analogs are phosphonomethylphenylalanine and mono- or difluorophosphonomethylphenylalanine. Peptide inhibitors of the invention can have homology with PTPase substrates. The sequence of these inhibitors can be based on the amino acid sequences of kinase autophosphorylation and endogenous substrate phosphorylation sites.

Phosphonomethylphenylalanyl peptides and mono- and difluorophosphonomethylphenylalanyl peptides constitute classes of compounds that potently inhibit PTPase activity. Pmp-peptides appear to act as direct substrate mimics, as binding affinity closely matches that of the corresponding phosphopeptides and inhibition is competitive. $F_2$Pmp peptides also appear to act as direct substrate mimics. However, binding affinity of the $F_2$Pmp-peptides can match or exceed that of the corresponding phosphopeptides. Inhibitors of the invention allow the inhibition of cellular PTPases and can be used in controlling metabolic processes, e.g., abnormal processes associated with diabetes, and as therapeutic modalities for selected malignancies. The inhibitors are also useful to study the enzymatic mechanisms of PTPase activity and to investigate the metabolic and biochemical roles of PTPases.

Signal transduction protein, as used herein, refers to a protein involved in transferring a signal from the cell surface into the cell and includes, e.g., membrane bound receptors, e.g., cell surface receptors, ligands of such receptors, and intracellular proteins which interact with either with a receptor, or with another intracellular protein to transfer a signal.

SH2 domain, as used herein, refers to a conserved apparently noncatalytic sequence of approximately 100 amino acids found in many signal transduction proteins including Fps, Stc, Abl, GAP, PLC$\lambda$, v-Crk, Nck, p85, and Vav. See Koch et al., 1991, Science 252:668, hereby incorporated by reference. The amino acid sequences of the SH2 domain of 27 proteins is given in Koch et al., 1991. The SH2 domain mediates protein-protein interactions between the SH2 containing protein and other proteins by recognition of a specific site on a second protein. The SH2/second protein site interaction usually results in an association of the SH2 contacting protein and the second protein. As used herein, SH2 domain refers to any sequence with at least 70%, preferably at least 80%, and more preferably at least 90% sequence homology with a naturally occurring SH2 domain, and to any analog or fragment of an SH2 domain which exhibits at least 50% of the binding activity of a naturally occurring variant of that domain, when binding is measured as the ability to bind a YFIN containing peptide.

Abnormal cell proliferation, as used herein, includes both neoplastic and non-neoplastic diseases, and thus includes diseases such as cancer and atherosclerosis.

A tissue sample as used herein means any suitable sample e.g., a sample including classic insulin sensitive tissue, e.g., muscle, fat or liver tissue, or a sample including more easily accessible tissue, e.g., circulating blood cells or fibroblasts.

A mutation, as used herein, means an alteration, either gross or small, in the nucleic acid which encodes $pp60^{PIK}$. Examples of common mutations are nucleotide deletions and insertions. The mutation further can be a mutation of the DNA encoding $pp60^{PIK}$ which results in misexpression of $pp60^{PIK}$.

A therapeutic agent, as used herein, can be any substance or treatment.

The metabolism of a substance, as used herein, means any aspect of the, expression, function, action, or regulation of the substance. The metabolism of a substance includes modifications, e.g., covalent or noncovalent modifications of the substance. The metabolism of a substance includes modifications, e.g., covalent or noncovalent modification, the substance induces in other substances. The metabolism of a substance also includes changes in the distribution of the substance. The metabolism of a substance includes changes the substance induces in the distribution of other substances.

An insulin-related disease, as used herein, is a disease, disorder, or condition in which some aspect of insulin expression, metabolism, or action is disrupted or, a disease in which insulin action contributes to the disease. An insulin resistant insulin related disease, as used herein, is any disease, disorder, or condition in which a normal amount of insulin results in a less than normal biological response. Examples of insulin resistant diseases include Type II diabetes, obesity, aging related insulin resistance, and insulin resistance that arises secondary to infections, hormonal disorders, or other causes.

A purified preparation of $pp60^{PIK}$, as used herein, means $pp60^{PIK}$ that has been separated from other proteins, lipids, and nucleic acids with which it naturally occurs. Preferably, the $pp60^{PIK}$ is also separated from substances, e.g., antibodies or gel matrix, e.g. polyacrylamide, which are used to purify it. Preferably, the purified preparation of $pp60^{PIK}$ constitutes at least 10% dry weight of the purified preparation. Preferably, the purified preparation contains sufficient $pp60^{PIK}$ to allow protein sequencing.

A substantially pure nucleic acid, e.g., a substantially pure DNA, is a nucleic acid which is one or both of: not immediately contiguous with both of the coding sequences with which it is immediately contiguous (i.e., one at the 5' end and one at the 3' end) in the naturally-occurring genome of the organism from which the nucleic acid is derived; or which is substantially free of a nucleic acid sequence with which it occurs in the organism from which the nucleic acid is derived. The term includes, for example, a recombinant DNA which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. Substantially pure DNA also includes a recombinant DNA which is part of a hybrid gene encoding additional $pp60^{PIK}$ sequence.

Homologous refers to the sequence similarity between two $pp60^{PIK}$ molecules or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared $\times 100$. For example, if 6 of 10, of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The terms peptides, proteins, and polypeptides are used interchangeably herein.

A transgene is defined as a piece of DNA which is inserted by artifice into a cell and becomes a part of the genome of an animal which develops in whole or part from that cell. Such a transgene may be partly or entirely heterologous to the transgenic animal. A transgene can include a deletion.

A peptide has $pp60^{PIK}$ biological activity if it has one or more of the following properties: 1. The peptide is capable of binding to IRS-1; 2. The peptide is capable of binding the PI 3'-kinase; 3. The peptide is capable of competitively inhibiting the binding of native $pp60^{PIK}$ to IRS-1; 4. The peptide is capable of inhibiting $pp60^{PIK}$ binding to PI 3'-kinase.

Misexpression, as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the size, amino acid sequence, post-transitional modification, or biological activity of pp60$^{PIK}$; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

A transgenic animal, e.g., a transgenic mouse, is an animal having cells that contain a transgene, which transgene was introduced into the animal, or an ancestor of the animal, at a prenatal, e.g., an embryonic, stage. A transgenic cell is a cell which includes a transgene.

A pp60$^{PIK}$ peptide is a peptide which is encoded by a nucleic acid of the invention, preferably it has at least 80% homology with native pp60$^{PIK}$ and has pp60$^{PIK}$ activity.

The phosphatidylinositol (PI) 3'-kinase is implicated in receptor-stimulated mitogenesis and differentiation, the oxidative burst in neutrophils, membrane ruffling and insulin-stimulated glucose transport. PI 3'-kinase is ordinarily composed of a 110 kDa catalytic subunit in association with an 85 kDa regulatory protein that contains two Src homology-2 (SH2) domains (p85). During insulin stimulation, the PI 3'-kinase is activated when phosphorylated YXXM (SEQ ID NO: 5) motifs in IRS-1 bind to the SH2 domains of p85. While screening an expression library for new SH2-proteins that bind to IRS-1, a new cDNA encoding a 60 kDa protein was isolated. This protein, pp60$^{PIK}$, contains two SH2 domains with similarity to p85, and forms a stable complex with the catalytic subunit of the PI 3'-kinase (p110). However, pp60$^{PIK}$ lacks the SH3 domain and the break chain region (BCR)-homology region of the p85s, and contains a unique and short amino terminus. During insulin stimulation, pp60$^{PIK}$ is tyrosine phosphorylated and the associated PI 3'-kinase is activated, which may provide a new pathway to regulate PI 3'-kinase.

EXAMPLES

Example 1

Figure 2:
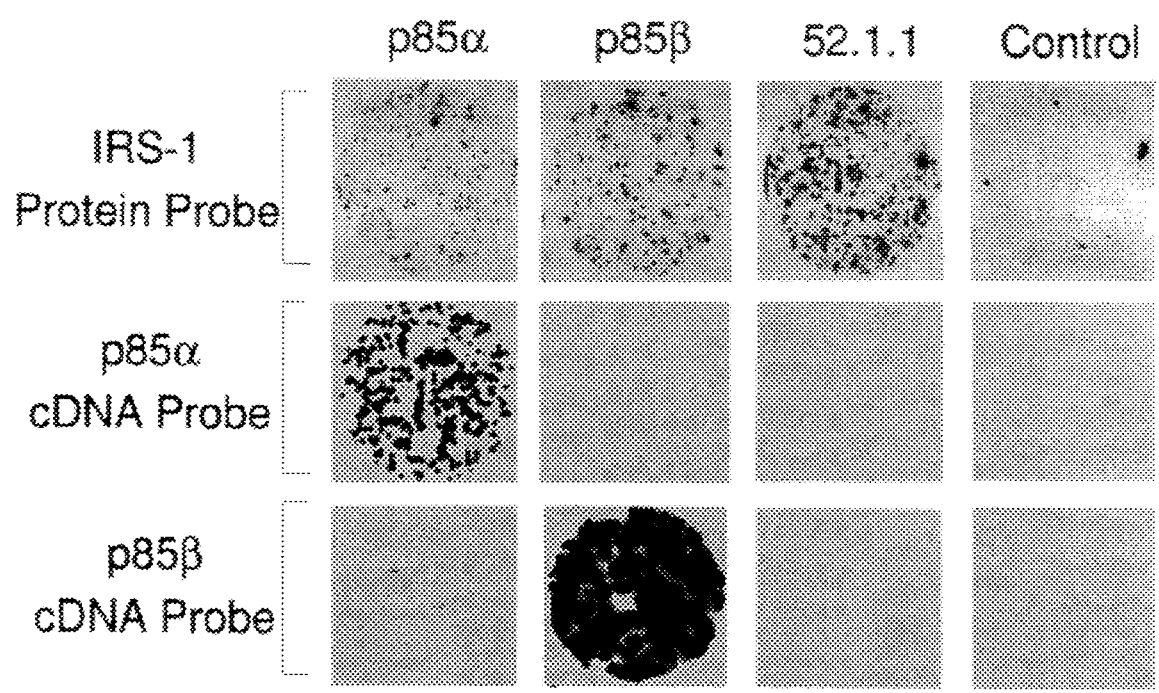
FIG. 2 is a depiction of the results of screening of a mouse adipocyte library using the following probes: IRS-1 protein probe, p85α cDNA probe, and p85β cDNA probe.

Isolation of cDNA encoding pp60$^{PIK}$ and Characterization of pp60$^{PIK}$ pp60$^{PIK}$ was identified in a mouse fat cDNA expression library by screening with recombinant [$^{32}$P]IRS-1. The cDNA was confirmed in a mouse embryo library by DNA screening. See FIG. 2.

Preparation of the [$^{32}$P]IRS-1 probe: IRS-1 has no extrinsic enzymatic activity. IRS-1 must, therefore, be labeled by incubation with an activated insulin receptor in the presence of [γ-$^{32}$P]ATP and Mn$^{2+}$. IRS-1 was obtained from Sf-9 cells infected with a recombinant baculovirus containing the cDNA of IRS-1. A 100 ml culture of Sf-9 cells yields approximately 1 mg of phosphotyrosine-free IRS-1 that is purified to >95% by gel exclusion chromatography on SK300HR (Pharmacia, Piscataway, N.J.). [$^{32}$P]IRS-1 is prepared by incubating IRS-1 with human insulin receptor partially purified from Chinese hamster ovary cells (CHO) expressing wild-type insulin receptor cDNA. The insulin receptor (5 mg of protein in a wheat germ agglutinin eluate) is activated by autophosphorylation during a twenty minute incubation with 100 nM insulin, 50 mM [γ-$^{32}$P]ATP (67,00 cpm/pmol, NEN) and 5 mM MnCl$_2$. IRS-1 (1 mg: 8 pmol) was added to the active kinase mixture and incubated at 4° C. overnight. The [$^{32}$P]IRS-1 in this reaction was immunoprecipitated completely with anti-phosphotyrosine antibody indicating that each labeled molecule contains phosphotyrosine. The [$^{32}$P]IRS-1 was reduced with 0.1M dithiothreitol in 50 mM Tris-HCl buffer (pH 7.4) containing 250 mM NaCl and 6M guanidinium chloride for five hours at 55° C., and then carboxymethylated with iodoacetamide (Pierce, Rockford, Ill.). The carboxymethylated and reduced [$^{32}$P] IRS-1 was washed several times in a Centricon-30 microconcentrator (Amicon, inc., Beverly, Mass.) with 10 mM Tris-HCl (pH 7.4) containing 50 mM NaCl to remove contaminating [γ-$^{32}$P]ATP. [$^{32}$P]IRS-1 is resuspended in 10 mM Tris-HCl (pH 8.0) containing 150 mM NaCl and 0.05% Tween 20 to a concentration of 2–5×10$^5$ cpm/ml for use as the probe.

Expression screening with recombinant [$^{32}$P]IRS-1: To identify IRS-1 binding proteins, an oligo(dT) primed subtraction library enriched with cDNA clones from F442a adipocytes was prepared in Uni-Zap XR as is known in the art. Adipose tissue was selected because it is a major site of insulin action in mammals. Recombinant [$^{32}$P]IRS-1 was used to screen F442a λZAP expression library (500,000 plaques) prepared from mRNA enriched with transcripts expressed in F442a adipose cells and depleted for transcripts predominant in undifferentiated F442a fibroblasts. The plates were incubated for 3.5 hours at 42° C., then overlaid with nitrocellulose filters (Millipore, HATF) that were impregnated with 10 mM isopropyl-b-D-thiogalactopyranoside (IPTG, BRL), and incubated for 10 hours at 37° C. The filters were removed, briefly washed TNT buffer (10 mM Tris-HCl), pH 8.0, 150 mM NaCl, 0.05% Tween 20) at room temperature, and then blocked in TNT buffer containing 5% Carnation instant dry milk for six hours. The filters were incubated overnight at 4° C. with [$^{32}$P]IRS-1 (50 mg/ml), and then washed three times at room temperature with 10 mM Tris-HCl, pH 8.0, 150 mM NaCl, 0.01% Tween 20. The dry filters were exposed to Kodak XAR-5 film with an intensifying screen at −70° C. for twenty-four hours. Thirty primary positive plaques were selected, and fifteen remained positive during subsequent hybridizations with [$^{32}$P]IRS-1. Fourteen hybridized strongly with a cDNA probe for p85α, whereas one (clone-52.1.1) was unique and did not cross-react with cDNA probes to p85α or p85β under ordinary screening conditions. See FIG. 2.

Figure 1A:
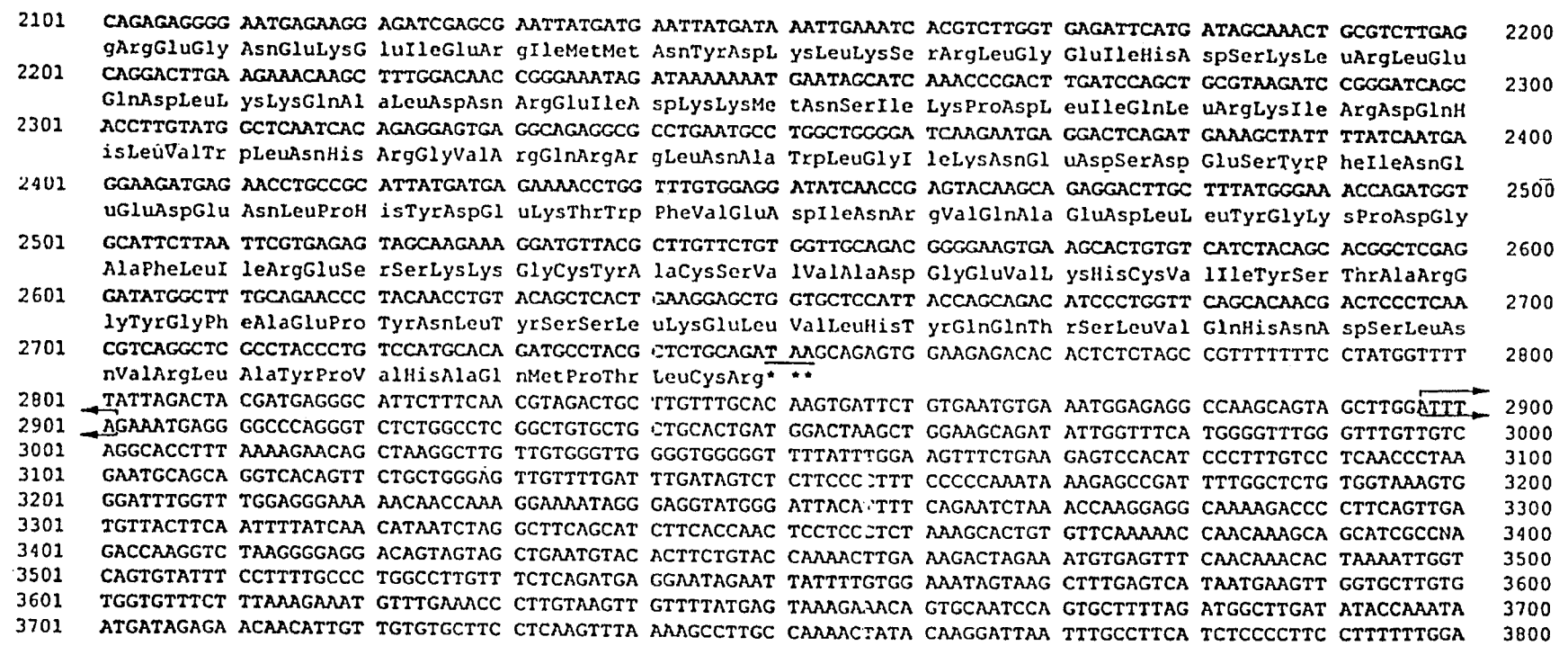
Figure 1B:
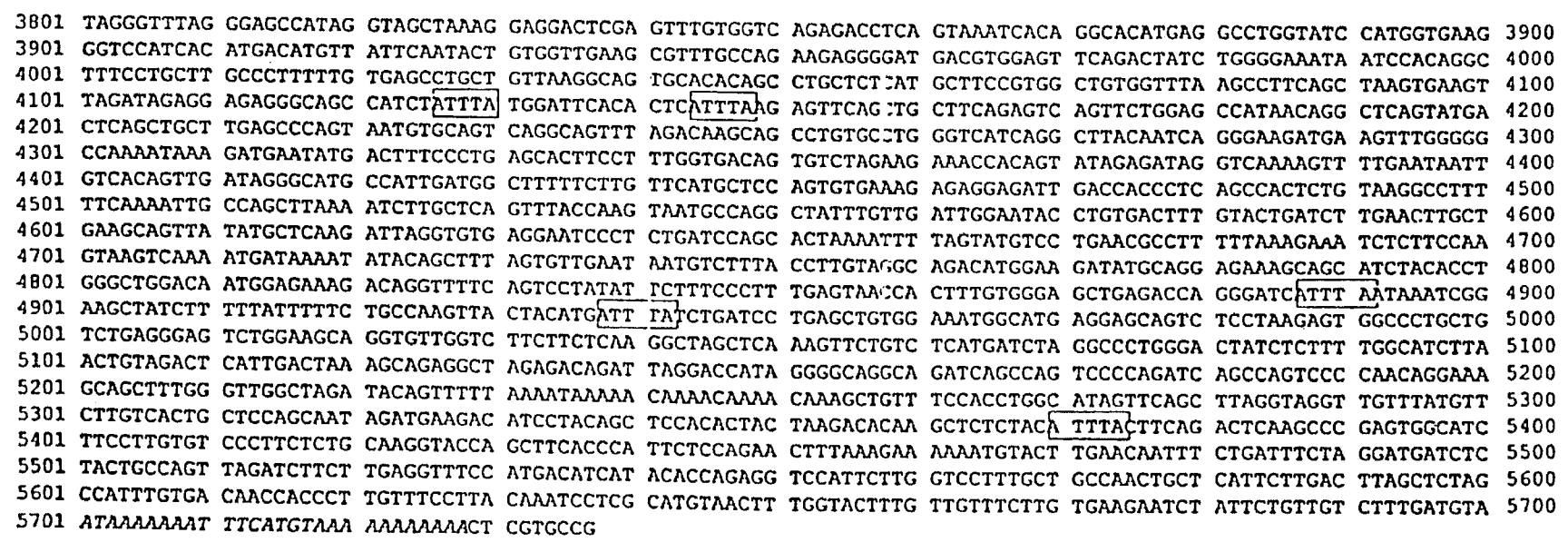
Figure 3:
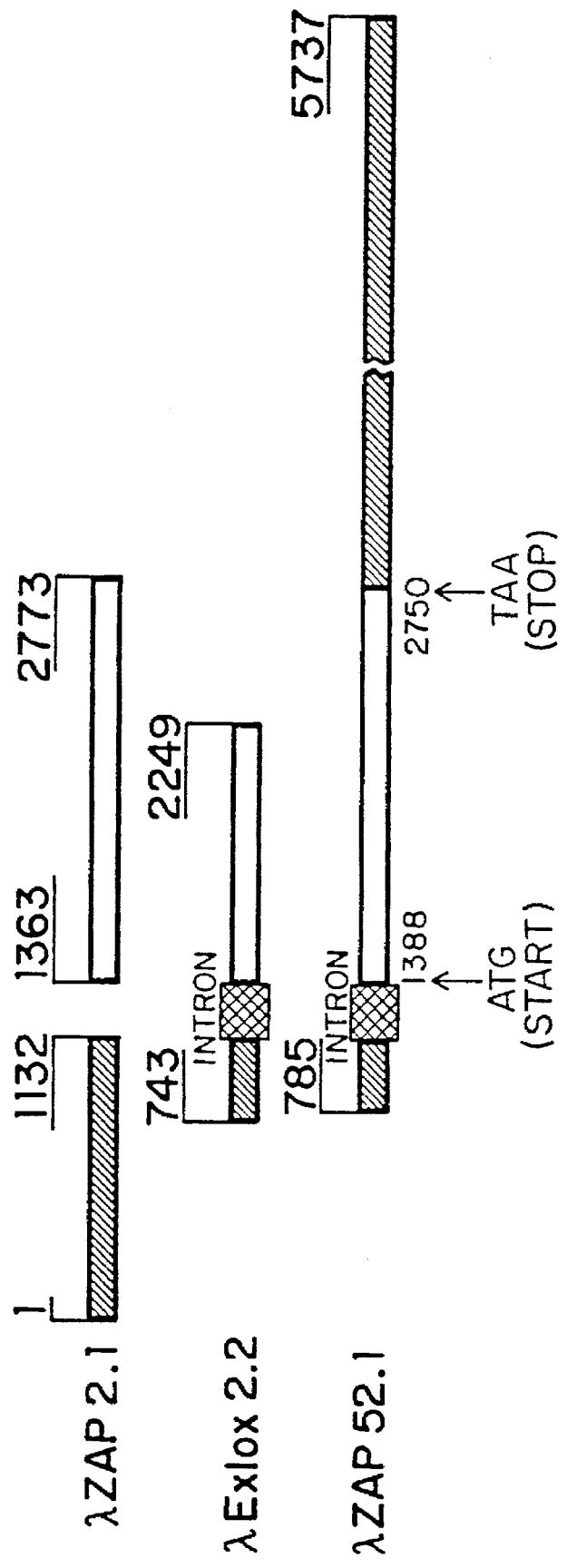
FIG. 3 is a schematic diagram of the three clones (λZAP 2.1, λExlox, λZAP 52.1) from which the DNA sequence of pp60$^{PIK}$ cDNA was derived.

A full length cDNA probe of clone 52.1.1 was used to screen the F442a λZAP library and a λExlox mouse embryo (day 13) library, which revealed two independent and strongly hybridizing clones (λZAP 2.1, and λExlox 2.2) (FIG. 3). Based on the complete DNA sequence of the three clones, a contiguous cDNA containing 5737 bases was obtained (FIG. 1). One of the clones (λZAP 2.1) contained an apparent deletion in the 5'-untranslated region, which is presumably derived from an alternative splicing event. The complete DNA sequence contains a 5'-untranslated region of 1366 bp, an open reading frame of 1383 bp, and a 3'-untranslated regions of 2987 bp with six putative mRNA destabilization motifs (ATTTA), and five polyadenylation signals (AATAAA).

The primary amino acid sequence encoded by the cDNA is related to the C-terminal half of the regulatory subunits of the phosphatidylinositol (PI)-kinase (FIG. 4). The open reading frame encodes a 461-amino acid sequence with two SH2 domains, one at its N-terminus (residues 65–163) and one at its C-terminus (residues 358–452). A Genebank search revealed a high homology at the protein level between pp60$^{PIK}$ and the carboxyl terminal half of p85α and p85β (FIG. 4). The N-terminal SH2 domain of pp60$^{PIK}$ was 88.9% and 83.8% identical to the corresponding region in p85α and p85β, respectively. The carboxy-terminal SH2 domain of pp60$^{PIK}$ was 81.1% and 73.7% identical to the corresponding region in p85α and p85β, respectively. Moreover, a region between the SH2 domains of p85α (residues 479–492) which is suggested to mediate the association between p85 and p110 is completely conserved in pp60$^{PIK}$ (residues 210–224). The SH3 domain or BCR (break chain region)-homology region ordinarily found in p85α or p85β is replaced in pp60$^{PIK}$ by a short unique amino terminus. Unlike, p85, pp60$^{PIK}$ is tyrosine phosphorylated at insulin stimulation (FIG. 4, tyrosine 341).

Example 2

Expression and distribution of pp60$^{PIK}$ in mouse tissue

Using a cDNA probe specific for pp60$^{PIK}$, northern analysis revealed a single mRNA species of 5.7 kb in most mouse tissues including liver, spleen, skeletal muscle, heart, kidney, fat, brain, and testes (FIG. 5, Panel A), indicating that the full length cDNA was isolated (FIG. 1). The relative expression of pp60$^{PIK}$ in these tissues was measured by competitive PCR (FIG. 5, Panel B). The mRNA for pp60$^{PIK}$ was isolated and translated into cDNA by reverse transcriptase and amplified by PCR in the presence of various concentrations of known quantities of pp60$^{PIK}$ cDNA containing a unique restriction site as an internal standard. The results of this analysis show that pp60$^{PIK}$ mRNA is most highly expressed in fat, brain, and testes, but detectable in kidney to a greater degree than in heart; and in heart to a greater degree than in skeletal muscle (FIG. 5, Panel B). By this analysis, the message for pp60$^{PIK}$ is expressed to the lowest degree in liver. The distribution of pp60$^{PIK}$ determined by competitive PCR was qualitatively similar to the northern analysis.

Example 3 pp60$^{PIK}$ associates with the catalytic subunit of PI 3'-kinase

Previous reports have suggested that a region between the SH2 domains of p85 binds the catalytic subunit of the PI 3'-kinase, p110. As shown in FIG. 4, this region is perfectly conserved in pp60$^{PIK}$. To investigate whether pp60$^{PIK}$ associates with the p110 catalytic subunit, the two proteins were expressed separately or together in Sf-9 cells. See FIG. 6. A cDNA (bases 1365–2656) encoding the complete N-terminal SH2 domain, the intra-SH2 domain, and a portion of the C-terminal SH2 domain of pp60$^{PIK}$ was subcloned into pBluebac vector and the baculovirus was obtained by its transfection to Sf-9 insect cells. The Sf-9 cells were infected with recombinant viruses and the PI kinase activity in pp60$^{PIK}$ and p110 immunoprecipitates was measured. The antibody against the N-terminal SH2 domain of p85α recognized pp60$^{PIK}$ because of a similar amino acid sequence between p85α and pp60$^{PIK}$. This antibody was used for immunoprecipitation and immunoblotting of pp60$^{PIK}$. The successful expression of pp60$^{PIK}$ and p110 by infection of pp60$^{PIK}$ virus and p110 virus was confirmed by Western blotting (FIG. 6). In double infections of baculoviruses expressing pp60$^{PIK}$ and p110, p110 was co-immunoprecipitated with pp60$^{PIK}$ by the antibody against the N-terminal SH2 domain of p85α. (FIG. 7) In addition, this immunoprecipitate was found to possess markedly higher PI 3'-kinase activity than other immunoprecipitates from the cells infected with either pp60$^{PIK}$ or p110. These results suggest that pp60$^{PIK}$ forms a stable complex with p110 catalytic subunit of PI 3'-kinase.

Example 4

Activation of PI 3'-kinase associated with pp60$^{PIK}$ during insulin stimulation FLAG-tag sequence was added by using polymerase chain reaction (PCR) to the C-terminal end of pp60$^{PIK}$ to distinguish pp60$^{PIK}$ from endogenous p85α. The cDNA encoding pp60$^{PIK}$ with FLAG-tag was subcloned into the CAGG expression vector. Parental CHO cells and CHO cells overexpressing insulin receptors (CHO/IR) were transfected with this expression vector and hygromycin-resistant DNA, and selected in the medium containing 300 µg/ml hygromycin B. As shown in FIG. 8, expressed pp60$^{PIK}$ was recognized by the FLAG-tag antibody with its molecular size of 63 kDa. In the CHO/IR cells overexpressing pp60$^{PIK}$, the association of pp60$^{PIK}$ with IRS-1 or insulin receptor were investigated in the presence or absence of insulin. In the presence of insulin, phosphorylated IRS-1 and insulin receptor were co-immunoprecipitated with pp60$^{PIK}$ by FLAG-tag antibody (FIG. 8), while no bands were observed from the control CHO/IR cells (data not shown). In addition, the immunoprecipitated pp60$^{PIK}$ was demonstrated to be phosphorylated at tyrosine residues by the addition of insulin, while no phosphorylation of endogenous p85α was detected under the same conditions (data not shown).

Example 5

Phosphorylation of pp60$^{PIK}$ by the insulin receptor pp60$^{PIK}$ was isolated from CHO cells expressing pp60$^{PIK}$ by immunoprecipitation with anti-FLAG antibodies. The immuncomplex was collected on protein A-Sepharose and washed in HEPES (50 mM, pH 7.5) containing 0.1% Triton. Partially purified insulin receptor was added to the immun-complex together with Mn$^{2+}$ (5 mM) and [γ-$^{32}$P]ATP. After incubation for thirty minutes, the phosphorylated proteins were separated by SDS-PAGE and transferred to nitrocellulose. A strong phosphoprotein was detected in a sample from the CHO cells expressing pp60$^{PIK}$, whereas a weak band was obtained from the control cells. (FIG. 9).

The nitrocellulose containing [$^{32}$P]labeled pp60$^{PIK}$ was excised and treated with 0.5% (w/v) PVP-40 (Sigma, St. Louis, Mo.) in 100 ml acetic acid for one hour at 37° C. The paper was then washed extensively with water and digest with 10 µg of TPCK-trypsin (Worthington, Freehold, N.J.) in NaHCO$_3$ (pH 8.0) containing acetonitrile at 37° C. for twenty-four hours. An additional 10 µg TPCK-trypsin was added, and the digestion was continued for an additional twenty-four hours. This technique consistently eluted 90–95% of the phosphopeptides. The trypsinization was terminated by the addition of sample buffer and boiling for three minutes. The phosphopeptides were separated by Tricine/SDS/PAGE using a 32-cm acrylamide gel consisting of a 3% stacker, 10% spacing, and 16.5% resolving gel. After electrophoresis, the gels were sealed with plastic wrap and exposed to film at −80° C. A single phosphopeptide was detected which contained exclusively phophotyrosine. This phosphopeptide was eluted from the Tricine/SDS/PAGE gel and dialyzed against water for forty-eight hours. The phosphopeptide was lyophilized and resuspended in 50% acetonitrile. A portion of the peptide sample was dissolved in water and digested with 7 µg of protease V8 of Asp-N (Boehringer Mannheim, Indianapolis, Ind.) for eighteen hours at 22° C. Peptide fragments were covalently coupled to Sequelon™ -AA discs (Millipore, Bedford, Mass.) with 1-ethyl-3-(3-dinthylaminopropyl)carbodiimide and washed extensively with water, methanol, and trifluoroacetic acid. Manual Edman degradation of the phosphopeptides was performed as follows. Briefly, immobilized peptides were reacted with 0.5 ml of coupling reagent (methanol:water triethylamine:phylisothiocyanate 7:1:1:1, v/v) at 55° C. for ten minutes and washed with methanol. Phenylthiohydantoin derivatives were eluted with 0.5 ml of trifluoroacetic acid (55° C., six minutes) followed by a wash with trifluoroacetic acid and 42.5% phosphoric acid (Sigma, St. Louis, Mo.; 9:1, v/v). The radioactivity released and associated with the disc was monitored by Cerenkx radiation. Edman degradation was repeated for the indicated number of times.

Example 6

Insulin stimulates tyrosine phosphorylation of $pp60^{PIK}$ at tyrosine 341

The insulin-stimulated phosphorylation site in $pp60^{PIK}$ was characterized by phosphoamino acid analysis, tryptic digestion, and manual Edman degradation to isolate the major site within the amino acid sequence. An immuncomplex containing $pp60^{PIK}$ was prepared by incubating extracts from quiescent CHO cells or CHO/$pp60^{PIK}$ cells with an anti-FLAG antibody. The immuncomplex was collected on protein-A-Sepharose, and $pp60^{PIK}$ was phosphorylated by a brief incubation with activated insulin receptors and [$^{32}$P] ATP (FIG. 9, left panel); phosphoamino acid analysis revealed that this was exclusively tyrosine phosphorylation (data not shown). Tryptic digestion of phosphorylated $pp60^{PIK}$ yields a single phosphorylated band following separation of the peptides by Tricine SDS-PAGE.

To determine the location of the phosphorylated tyrosine in the $pp60^{PIK}$ sequence, the tryptic fragment was characterized by additional digestion with V8 protease or endo-Asp-N. The original tryptic peptide and the products of these additional digests were immobilized on disks and subjected to manual Edman degradation. Radioactive phosphate was released from the tryptic peptide after cycle 8, where radioactivity was released after cycles 2 or 4 from the V8 and endo-Asp-N secondary digests, respectively. This pattern of digestion unambigously predicts the phosphorylation of Tyr-341 in the $pp60^{PIK}$ molecule. See FIG. 10.

Example 7

Effect of insulin on PI 3'-kinase activity on chinese hamster ovary (CHO) cells overexpressing $pp60^{PIK}$ The effect of insulin on PI 3'-kinase activity on chinese hamster ovary (CHO) cells overexpressing $pp60^{PIK}$ was examined. See FIG. 11. The expression level of $pp60^{PIK}$ in CHO/IR/$pp60^{PIK}$ was very similar to that of $pp60^{PIK}$ in CHO/$pp60^{PIK}$. Various concentrations of insulin were added and PI 3'-kinase activity in the immunoprecipitates by FLAG-tag antibody or IRS-1 antibody were measured (FIG. 11). As shown in FIG. 10, FLAG-tag antibody recognized $pp60^{PIK}$, but not endogenous p85. Stimulation of CHO/$pp60^{PIK}$ and CHO/IR/$pp60^{PIK}$ with saturating insulin concentrations increased PI 3'-kinase activity 1.5 fold and 5 fold.

Autophosphorylation contributes to the activation of the insulin and insulin-like growth factor (IGF-1) receptors, but it does not appear to mediate SH2-protein binding. This pathway was first illustrated for the phosphatidylinositol 3'-kinase, which is activated during its association with phosphorylated IRS-1.

Most tyrosine kinase receptors mediate biological responses by using their tyrosine autophosphorylation sites to engage downstream signaling molecules with Src-homology-2 domains (SH2-proteins). EGF and PDGF receptors undergo a ligand-induced autophosphorylation at multiple tyrosine residues which associate directly with various SH2 proteins, including phosphatidylinositol 3'-kinase, p 21$^{ras}$GAP, phospholipase Cγ, GRB-2, c-fyn, c-src, and probably other SH2-proteins. In contrast, these receptors phosphorylate an intermediate adapter molecule, IRS-1, which directly associates with multiple SH2-proteins. Instead, these receptors phosphorylate intermediate "docking proteins" such as IRS-1 or 4PS, which function as tyrosine phosphorylated docking protein to recruit the SH2-proteins into a signaling complex. The interleukin-4 receptor (IL-4r) illustrates an additional complexity since it phosphorylates IRS-1 even though it does not contain an intrinsic tyrosine kinase activity. The IL-4r, like other receptors in the hematopoietic family such as those for erythropoeitin, growth hormone and interferon, presumably recruit cytoplasmic tyrosine kinases, possibly similar to JAK-1, tyk-2, fyn, into a multimerit signaling complex to phosphorylate IRS-1 or related docking elements.

In addition to IRS-1 and other 180 kDa substrates described above, a number of other lower molecular weight proteins become tyrosine-phosphorylated in insulin-treated cells. A 60 kDa tyrosine-phosphorylated protein has been observed in several laboratories after insulin treatment of primary rat adipocytes and Chinese hamster ovary cells expressing human insulin receptors. More recently, a 60 kDa tyrosine-phosphorylated protein has been observed in p 21$^{ras}$GAP or PI 3'-kinase immunoprecipitates.

During insulin stimulation of rat adipocytes, $pp60^{PIK}$ associates with the PI 3'-kinase in a complex that appears to be distinct from IRS-1. The $pp60^{PIK}$:PI 3'-kinase complex was located in both the soluble and membrane fractions, whereas IRS-1 was entirely cytosolic. Since recombinant SH2 domains of p85 precipitate $pp60^{PIK}$ from insulin-stimulated cells, Levan and Lienhard concluded that the most likely mode of association of $pp60^{PIK}$ with PI 3'-kinase is through the binding of its tyrosine phosphorylation site to p85. By affinity chromatography using immobilized phosphotyrosine antibody, $pp60^{PIK}$ was obtained in high percentage yield from insulin-stimulated rat adipocytes, but the low amount of the protein obtained (about 3 ng form the adipocytes of one rat) precluded sequence analysis.

An additional 60 kDa substrate exists for the insulin receptor. This protein associates with p21$^{ras}$GAP and appears to be distinct from the better known GAP-associated protein, pp62. This protein is particularly interesting because it is a potential link between the insulin receptor and the ras signaling system. Ras, a monomeric membrane-bound GTP-binding protein, may be a downstream element in the insulin receptor signaling pathway which mediates certain biological functions. Insulin stimulates the accumulation of activated rasGTP in cells, and appears to play a role in insulin-stimulated Glut-4 translocation. Moreover, microinjection of anti-ras antibodies inhibits insulin-induced maturation of Xenopus oocytes and overexpression of a dominant inhibitory ras mutant blocks insulin action on both gene expression and differentiation of 3T3-L1 to adipocytes. Thus, 60 kDa substrates of the insulin receptor are implicated in two important signaling pathways, the PI 3'-kinase and the p21$^{ras}$ signaling pathways. The molecular structure of a 60 kDa insulin receptor substrate, pp60$^{PIK}$, which partially resembles the better known p85 is described herein.

Use

The peptides or nucleic acids of the invention may be administered to a mammal, particularly a human, in one of the traditional modes (e.g., orally, paternally, transdermally, or transmucosally), in a sustained release formulation using a biodegradable biocompatible polymer, or by on-site delivery using micelles, pumps, e.g., osmotic drug delivery pumps, gels and liposomes or by transgenic modes.

Other Embodiments

Included in the invention are: allelic variations; natural mutants; induced mutants; proteins encoded by DNA that hybridizes under high or low stringency conditions to a nucleic acid which encodes the peptide of SEQ ID NO:1 (for definitions of high and low stringency see Current Protocols in Molecular Biology, John Wiley & Sons, New York, 1989, 6.3.1–6.3.6, hereby incorporated by reference); and, peptides or proteins specifically bound by antisera to pp60$^{PIK}$, especially by antisera to an active site or binding domain of pp60$^{PIK}$. Also included are chimeric pp60$^{PIK}$s that include a pp60$^{PIK}$ peptide or protein and a second peptide, e.g., a toxin, e.g., a chimeric molecule.

The invention also includes biologically active fragments or analogs of pp60$^{PIK}$. A biologically active fragment or analog is one having any in vivo or in vitro activity which is characteristic of the pp60$^{PIK}$ shown in SEQ ID NO1, e.g., one or more of the biological activities described above. Because peptides such as pp60$^{PIK}$ often exhibit a range of physiological properties and because such properties may be attributable to different portions of the molecule, a useful pp60$^{PIK}$ fragment or pp60$^{PIK}$ analog is one which exhibits a biological activity in any biological assay for pp60$^{PIK}$ activity. Most preferably the fragment or analog possesses 10%, preferably 40%, or at least 90% of the activity of pp60$^{PIK}$ (SEQ ID NO1), in any in vivo or in vitro pp60$^{PIK}$ assay.

Analogs can differ from naturally occurring pp60$^{PIK}$ in amino acid sequence or in ways that do not involve sequence, or both. Analogs of the invention will generally exhibit at least 90%, preferably 95% or even 99%, homology with a segment of 20 amino acid residues, preferably more than 40 amino acid residues, or more preferably the entire sequence of a naturally occurring pp60$^{PIK}$ sequence. Non-sequence modifications include in vivo or in vitro chemical derivatization of pp60$^{PIK}$s. Non-sequence modifications include changes in acetylation, methylation, phosphorylation, carboxylation, or glycosylation. Glycosylation can be modified, e.g., by modifying the glycosylation patterns of a pp60$^{PIK}$ during its synthesis and processing or in further processing steps, e.g., by exposing the pp60$^{PIK}$ to glycosylation affecting enzymes derived from cells that normally provide such processing, e.g., mammalian glycosylation enzymes; phosphorylation can be modified by exposing the pp60$^{PIK}$ to phosphorylation-altering enzymes, e.g., kinases or phosphatases.

Preferred analogs include pp60$^{PIK}$ (or biologically active fragments thereof) whose sequences differ from the wild-type sequence by one or more conservative amino acid substitutions or by one or more non-conservative amino acid substitutions, deletions, or insertions which do not abolish the pp60$^{PIK}$'s biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

TABLE 1

CONSERVATIVE AMINO ACID REPLACEMENTS

| For Amino Acid | Code | Replace with any of |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp; Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Other analogs within the invention are those with modifications which increase peptide stability; such analogs may contain, for example, one or more non-peptide bonds (which replace the peptide bonds) in the peptide sequence. Also included are: analogs that include residues other than naturally occurring L-amino acids, e.g., D-amino acids or non-naturally occurring or synthetic amino acids, e.g., β or γ amino acids; and cyclic analogs.

As used herein, the term "fragment", as applied to a pp60$^{PIK}$, will ordinarily be at least about 20 residues, more typically at least about 40 residues, preferably at least about 60 residues in length. Fragments of pp60$^{PIK}$ can be generated by methods known to those skilled in the art. The ability of a candidate fragment to exhibit a biological activity of pp60$^{PIK}$ can be assessed by methods known to those skilled in the art as described herein. Also included are pp60$^{PIK}$'s containing residues that are not required for biological activity of the peptide or that result from alternative mRNA splicing or alternative protein processing events.

Also within the invention are: a purified antibody preparation, preferably a monoclonal antibody preparation, directed against a protein or peptide of the invention.

Nucleic acid encoding all or part of the pp60$^{PIK}$ gene can be used to transform cells. For example, the pp60$^{PIK}$ gene, e.g., a misexpressing or mutant form of it e.g., a deletion, or other DNA encoding an pp60$^{PIK}$ protein or peptide can be used to transform a cell and to produce a cell in which the cell's genomic pp60$^{PIK}$ gene has been replaced by the transformed gene, producing, e.g., a cell deleted for the pp60$^{PIK}$ gene. This approach can be used with cells capable of being grown in culture, e.g., cultured stem cells, to investigate the function of the gene.

Analogously, nucleic acid encoding all or part of the pp60$^{PIK}$ gene, e.g., a misexpressing or mutant form of the gene, e.g., a deletion, can be used to transform a cell which subsequently gives rise to a transgenic animal, e.g. a transgenic mouse. This approach can be used to create, e.g., a transgenic animal in which the pp60$^{PIK}$ gene is, e.g., inactivated, e.g., by a deletion. Homozygous transgenic animals can be made by crosses between the offspring of a founder transgenic animal. Cell or tissue cultures can be derived from a transgenic animal.

In order to obtain a pp60$^{PIK}$ peptide, pp60$^{PIK}$-encoding DNA is introduced into an expression vector, the vector introduced into a cell suitable for expression of the desired protein, and the peptide recovered and purified, by prior art methods. Antibodies to the peptides an proteins can be made by immunizing an animal, e.g., a rabbit or mouse, and recovering anti-pp60$^{PIK}$ antibodies by prior art methods.

Fragments of pp60$^{PIK}$ can be made by expressing pp60$^{PIK}$ DNA which has been manipulated in vitro to encode the desired fragment; e.g., by restriction digestion of the DNA sequence of SEQ ID NO:1. Analogs can be made, e.g., by in vitro DNA sequence modifications of the sequence of SEQ ID NO:1. For example, in vitro mutagenesis can be used to convert the DNA sequence of SEQ ID NO:1 into a sequence which encodes an analog in which one or more amino acid residues has undergone a replacement, e.g., a conservative replacement as described in Table 1. Fragments or analogs can be tested by methods known to those skilled in the art for the presence of pp60$^{PIK}$ activity.

The invention also provides for the generation of pp60$^{PIK}$ mimetics, e.g. peptides or non-peptide agents, which are able to modulate, e.g., inhibit, binding of a pp60$^{PIK}$ to another protein. Various forms of mutagenesis are generally applicable for mapping the determinants of the pp60$^{PIK}$ which participate in protein-protein interactions involved in binding to a second protein. For example, homologs of pp60$^{PIK}$ (both agonist and antagonist forms) can be generated and screened using, for example, alanine scanning mutagenesis and the like (Ruf et al. (1994) *Biochemistry* 33: 1565–1572; Wang et al. (1994) *J Biol Chem* 269:3095–3099; Balint et al. (1993) *Gene* 137:109–118; Grodberg et al. (1993) *Eur J Biochem* 218:597–601; Nagashima et al. (1993) *J Biol Chem* 268:2888–2892; Lowman et al. (1991) *Biochemistry* 30: 10832–10838; and Cunningham et al. (1989) *Science* 244:1081–1085), by linker scanning mutagenesis (Gustin et al. (1993) *Virology* 193:653–660; Brown et al. (1992) *Mol Cell Biol* 12:2644–2652; McKnight et al. (1982) *Science* 232:316); or by saturation mutagenesis (Meyers et al. (1986) *Science* 232:613).

The critical residues of peptides of the invention which are involved in molecular recognition of e.g., an SH2 domain, can be determined and used to generate peptidomimetics which competitively inhibit binding of pp60$^{PIK}$ with other proteins (see, for example, "*Peptide inhibitors of human papillomavirus protein binding to retinoblastoma gene protein*" European patent applications EP-412,7624 and EP-531,080A). By employing, for example, scanning mutagenesis to map the residues of pp60$^{PIK}$ involved in its binding to the another protein, peptidomimetic compounds can be generated which mimic those residues of pp60$^{PIK}$ ascertained to be involved in binding to the other protein, and which therefore can be used to inhibit binding of the authentic pp60$^{PIK}$ protein to the protein. For instance, non-hydrolyzable peptide analogs of such residues can be generated using benzodiazepine (e.g., see Freidinger et at. in *Peptides: Chemistry and Biology*, G. R. Marshall ed., ESCOM Publisher: Leiden, Netherlands, 1988), azepine (e.g., see Huffman et at. in *Peptides: Chemistry and Biology*, G. R. Marshall ed., ESCOM Publisher: Leiden, Netherlands, 1988), substituted gama lactam rings (Garvey et al. in *Peptides: Chemistry and Biology*, G. R. Marshall ed., ESCOM Publisher: Leiden, Netherlands, 1988), keto-methylene pseudopeptides (Ewenson et at. (1986) *J Med Chem* 29:295; and Ewenson et al. in *Peptides: Structure and Function* (Proceedings of the 9th American Peptide Symposium) Pierce Chemical Co. Rockland, Ill., 1985), β-turn dipeptide cores (Nagai et at. (1985) *Tetrahedron Lett* 26:647; and Sato et al. (1986) *J Chem Soc Perkin Trans* 1:1231), and β-aminoalcohols (Gordon et at. (1985) *Biochem Biophys Res Commun* 126:419; and Dann et at. (1986) *Biochem Biophys Res Commun* 134:71).

Other embodiments are within the following claims.

What is claimed is:

1. A substantially pure nucleic acid comprising a sequence encoding a pp60$^{PIK}$ peptide of SEQ ID NO:2.

2. A cell containing the nucleic acid of claim 1.

3. A method for manufacture of pp60$^{PIK}$ comprising culturing the cell of claim 2 in a medium to express said pp60$^{PIK}$.

4. A substantially pure nucleic acid encoding a fragment of the pp60$^{PIK}$ polypeptide of SEQ ID NO:2 having at least 40 amino acid residues in length.

5. The nucleic acid of claim 4, wherein said fragment is at least 50 amino acid residues in length.

6. The nucleic acid of claim 4, wherein said fragment is at least 60 amino acid residues in length.

7. A substantially pure nucleic acid encoding a polypeptide having at least 80% sequence identity with the pp60$^{PIK}$ polypeptide of SEQ ID NO:2 and having one or more of the following properties: 1) binding to IRS-2, 2) binding the PI 3'-kinase, 3) competitively inhibiting the binding of native pp60$^{PIK}$ to IRS-1, or 4) inhibiting pp60$^{PIK}$ binding to 3'-kinase.

8. The nucleic acid of claim 7, wherein said encoded polypeptide has at least 90% homology to SEQ ID NO:2.

9. The nucleic acid of claim 7, wherein said encoded polypeptide has at least 95% homology to SEQ ID NO:2.

10. The nucleic acid of claim 7, wherein said encoded polypeptide has at least 99% homology to SEQ ID NO:2.

11. A substantially pure nucleic acid encoding a pp60$^{PIK}$ polypeptide of SEQ ID NO:2 produced by the method comprising: culturing a cell which includes said nucleic acid in a medium to express said pp60$^{PIK}$.

* * * * *